United States Patent
Hopkins et al.

(10) Patent No.: US 6,841,563 B1
(45) Date of Patent: Jan. 11, 2005

(54) ARYLOXY PROPANOLAMINES FOR IMPROVING LIVESTOCK PRODUCTION

(75) Inventors: Randall Bruce Hopkins, Indianapolis, IN (US); Deana Lori Hancock, Carthage, IN (US); Michael Eugene Quimby, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 61 days.

(21) Appl. No.: 10/111,267

(22) PCT Filed: Nov. 13, 2000

(86) PCT No.: PCT/US00/31060

§ 371 (c)(1),
(2), (4) Date: Apr. 17, 2002

(87) PCT Pub. No.: WO01/36413

PCT Pub. Date: May 25, 2001

Related U.S. Application Data

(60) Provisional application No. 60/165,460, filed on Nov. 15, 1999.

(51) Int. Cl.$^7$ .................. A61K 31/4439; C07D 401/12; A61P 43/00
(52) U.S. Cl. ........................ 514/339; 514/338; 514/381; 514/359; 514/403; 514/415; 546/277.4; 546/275.7; 546/273.7; 546/268.4; 548/306.1; 548/361.1; 548/503; 548/259
(58) Field of Search .................. 546/277.4, 275.7, 546/273.7, 268.4; 548/306.4, 307.1, 361.1, 503, 259; 514/339, 338, 381, 403, 415, 359

(56) References Cited

U.S. PATENT DOCUMENTS

| | | | |
|---|---|---|---|
| 5,808,080 A | | 9/1998 | Crowell et al. |
| 5,840,738 A | * | 11/1998 | Bell et al. ................ 514/359 |
| 6,046,227 A | * | 4/2000 | Crowell et al. ............ 514/407 |
| 6,060,492 A | * | 5/2000 | Bell et al. ................ 514/359 |
| 6,075,040 A | * | 6/2000 | Bell et al. ................ 514/362 |
| 6,093,735 A | * | 7/2000 | Bell et al. ................ 514/338 |
| 6,140,352 A | * | 10/2000 | Crowell et al. ............ 514/339 |
| 6,534,504 B1 | * | 3/2003 | Hancock et al. .......... 514/234.5 |
| 6,617,347 B1 | * | 9/2003 | Crowell et al. ............ 514/407 |

FOREIGN PATENT DOCUMENTS

| | | |
|---|---|---|
| WO | WO 97 10825 A | 3/1997 |
| WO | WO 98 09625 A | 3/1998 |
| WO | WO 99 29673 A | 6/1999 |

* cited by examiner

*Primary Examiner*—Evelyn Mei Huang
(74) *Attorney, Agent, or Firm*—John C. Demeter

(57) ABSTRACT

Disclosed is a compound represented by structural formula (I): R1 is a substituted or unsubstituted aryl group. R2 and R3 are independently —H, a C1–C4 straight chained or branched alkyl group. R4 and R5 are independently —H, a C1–C4 straight chained or branched alkyl group or, taken together with the nitrogen atom to which each is bonded, a non-aromatic heterocyclic ring. Ring A and Ring B are independently further substituted with zero, one or two substituents. Physiologically acceptable salts of structural formula shown above are also included. Also disclosed is a method promoting growth, efficiency of feed utilization and/or production of lean body mass in a livestock animal. The method comprises administering to the animal an effective amount of one or more compounds represented by the structural formula as shown or a physiologically acceptable salt thereof.

22 Claims, 4 Drawing Sheets

Average Daily Gain

Feed Efficiency Ratio

Hot Carcass Weight

Adjusted 12th Rib Fat Thickness

Average Ribeye Area

Carcass Soft Tissue Composition[a,b]

Calculated Yield Grade

Conformation Score

ARYLOXY PROPANOLAMINES FOR IMPROVING LIVESTOCK PRODUCTION

This application is the National Stage of International Application No. PCT/US00/31060, filed Nov. 13, 2000, which claims the benefit of U.S. Provisional Application No. 06/165,460, filed Nov. 15, 1999.

BACKGROUND OF THE INVENTION

An important goal in animal husbandry is to develop biologically active agents which can increase the quantity and improve the quality of meat obtained from livestock animals.

"Increasing the quantity" of food obtained from livestock animals refers to, inter alia, promoting the growth of livestock animals, increasing the efficiency of feed utilized in raising livestock animals and/or enhancing the production of lean body mass in livestock animals. Biologically active agents which cause these effects are, commonly referred to as "anabolic agents".

"Improving the quality" of food obtained from livestock animals refers to, inter alia, reducing the quantity of subcutaneous fat in meat while at the same time retaining intramuscular fat. Subcutaneous fat, commonly referred to as "trim fat", can cause elevated cholesterol and/or triglyceride levels in individuals who consume large quantities of meat, has minimal nutritional value, and decreases the overall yield of meat. Therefore, the reduction or elimination of this type of fat from meat is desirable. On the other hand, intramuscular fat, commonly referred to as "marbling", contributes positively to the flavor of meat and maintains a high Quality Grade. Marbling is a therefore desirable quality. Biologically active agents which are modestly lipolytic can reduce subcutaneous fat while retaining the intramuscular fat.

Certain publications have appeared generally disclosing arylpropanolamines such as U.S. Pat. No. 5,013,761 and WO 97/10825. There is, however, a need for biologically active agents which are both strongly anabolic and modestly lipolytic. Biologically active agents with these properties can be administered to livestock to improve the economics of meat production by increasing the yield of meat (improved Yield Grade). Biologically active agents with these properties can also increase the profitability of meat production by producing meat with a high Quality Grade which, because it is healthier to consume yet retains its flavor, can command high prices from meat packers and consumers.

SUMMARY OF THE INVENTION

It has now been found that the presence of a carboxamide group at the two-position of Ring B in the aryloxy propanolamine represented by Structural Formula (I), shown hereinbelow, results in a compound which is strongly anabolic. The corresponding regioisomer with the carboxamide group in the four-position is significantly less anabolic. For example, the percent decrease in serum urea nitrogen level (SUN), which is indicative of anabolic effect, in cattle treated with the 2-carboxamide regioisomers is greater than in animals treated with the corresponding 4-carboxamide regioisomers (see Table 1 in Example 17). In addition, cattle treated with the 2-carboxamide regioisomers show modest increases in non-esterified fatty acid levels (NEFA), which is indicative of lipolytic effects, whereas cattle treated with 4-carboxamide regioisomers generally show much stronger increases (see Table 1 in Example 17).

In addition, it has now been found that the presence of a carboxamide group at the two-position of Ring B in the aryloxy propanolamine represented by Structural Formula (I), shown hereinbelow, results in a compound which significantly increases weight gain in male broiler chickens when administered during a 28 day feeding period, particularly days 35–49 of their life cycle (see Table 4 in Example 20). Moreover, a trend was observed towards improved feed efficiency during the entire 28-day feeding period. Finally, for treated birds, significant increases relative to a control were shown for the following carcass parameters: hot carcass weights; bone-in, skin-on, leg-quarter weights; and bone-in, skin-on, breast weight (see Table 4 in Example 20).

Based on these results, novel compounds and novel methods of improving meat production from livestock animals are disclosed herein.

One embodiment of the present invention is a compound represented by Structural Formula (I):

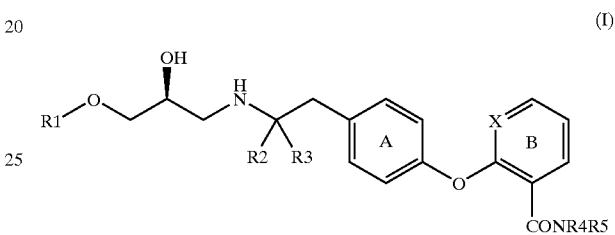

and physiologically acceptable salts thereof; where

R1 is a substituted or unsubstituted aryl group, provided, however, that when —X— is —CH—, then R1 is not a substituted or unsubstituted carbazolyl group;

R2 and R3 are independently —H, a C1–C4 straight chained or branched alkyl group;

R4 and R5 are independently —H, a C1–C4 straight chained or branched alkyl group or, taken together with the nitrogen atom to which each is bonded, a non-aromatic heterocyclic ring;

X is —N— or —CH—; and

Ring A and Ring B are independently further substituted with zero, one or two substituents.

Another embodiment of the present invention is a compound represented by Structural Formula (II):

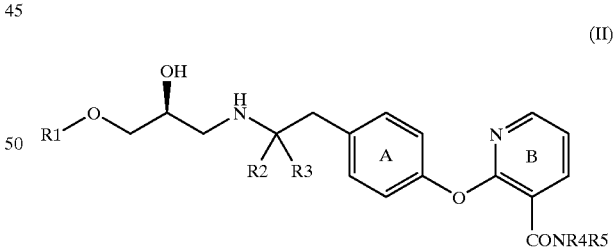

and physiologically acceptable salts thereof.

R1 in Structural Formula (II) is a substituted or unsubstituted aryl group; and R2–R5 and Rings A–B in Structural Formula (II) are as described above for Structural Formula (I).

Another embodiment of the present invention is a method of increasing the quantity and improving the quality of meat obtained from a livestock animal. The method comprises administering to the animal an effective amount of one or more compounds represented by Structural Formula (I) or (II) or a physiologically acceptable salt of a compound represented by Structural Formula (I) or (II).

The compounds of the present invention are strongly anabolic and modestly lipolytic. As a consequence, these compounds can be administered to livestock to increase the quantity of meat obtained from the animals. They also improve the quality of meat by reducing the amount of subcutaneous fat while retaining the intramuscular fat. Thus, the compounds of the present invention can be used to produce greater quantities of meat which is more healthy to consume and retains the normal flavor, i.e., retains marbling and a high quality grade, and can thereby increase the profitability of meat production. The compounds of the present invention are intended for the treatment of healthy animals.

DETAILED DESCRIPTION OF THE INVENTION

Figure 1:
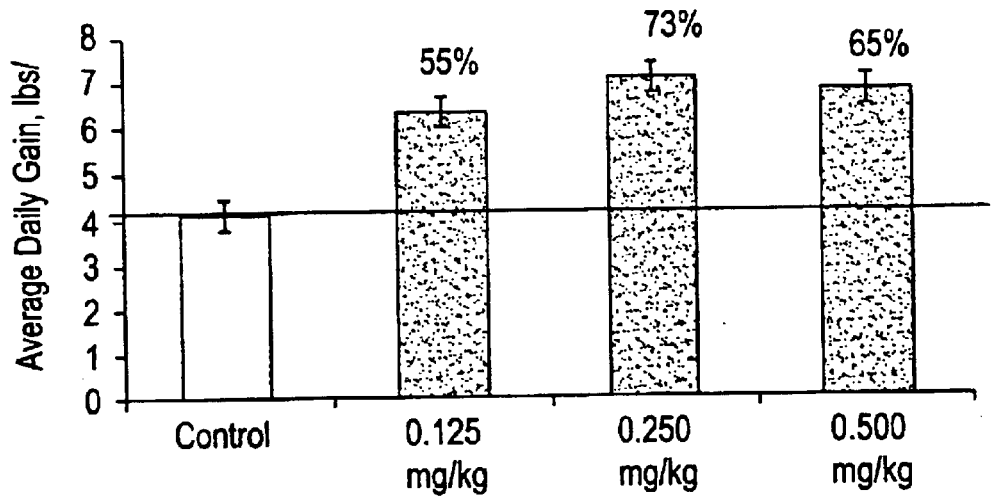
FIG. 1 is a graph showing the average daily weight gain after twenty-eight days of cattle treated with: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.

The present invention is directed to a compound represented by Structural Formula (I) or (II). Also included is a method of improving livestock production by administering one or more compounds of the present invention to the livestock.

In a preferred embodiment the compounds of the present invention are represented by Structural Formula (III):

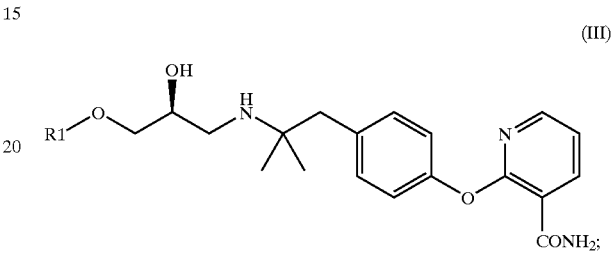

(III)

$R_1$ is as defined above for Structural Formula (II). Preferably, $R_1$ is represented by Structural Formula (IV), (V), (VI), (VII) or (VIII):

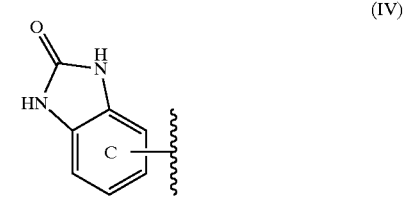

(IV)

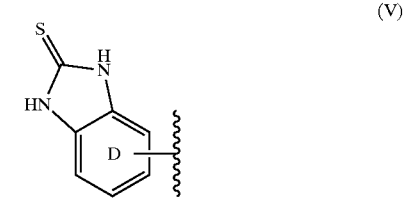

(V)

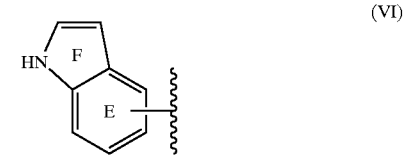

(VI)

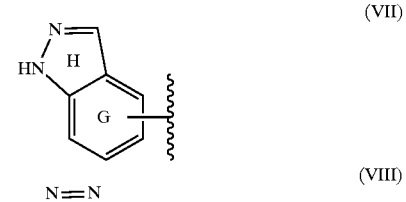

(VII)

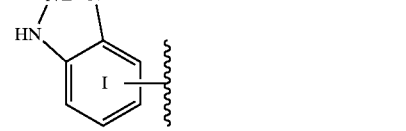

(VIII)

Ring C through Ring I are independently substituted or unsubstituted. Preferably, Rings C through Ring I are unsubstituted.

Aryl groups include carbocyclic aromatic groups such as phenyl, 1-naphthyl, 2-naphthyl, 1-anthracyl and 2-anthracyl, and heteroaryl groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aryl groups also include fused polycyclic aromatic ring systems in which a carbocyclic aromatic ring or heteroaryl ring is fused to one or more other heteroaryl rings. Examples include 1-benzimidazolinyl, 2-benzimidazolonyl, 1-benzimidthioazolinyl, 2-benzimidthioazolonyl, 1-carbazolyl, 2-carbazolyl, 3-carbazolyl, 4-carbazolyl, 3-indazolyl, 4-indazolyl, 5-indazolyl, 6-indazolyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 2-quinolinyl, 3-quinolinyl, 1-isoquinolinyl, 3-quinolinyl, 1-isoindolyl and 3-isoindolyl. Also included within the scope of the term aryl group, as it is used herein, is a group in which one or more carbocyclic aromatic rings and/or heteroaromatic rings are fused to a cycloalkyl or non-aromatic heterocyclic ring.

Non-aromatic heterocyclic rings are non-aromatic carbocyclic rings which include one, two or three heteroatoms selected from nitrogen, oxygen and sulfur in the ring that will afford a stable structure. The ring can be five, six, seven or eight-membered. Examples include 2-tetrahydrofuranyl, 3-tetrahydrofuranyl, 2-tetrahyrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl.

As used herein, aliphatic groups include straight chained, branched or cyclic C1–C20 hydrocarbons which are completely saturated or which contain one, two or three units of unsaturation.

Suitable substituents on an aliphatic group, aryl group (carbocyclic and heteroaryl), non-aromatic heterocyclic ring or benzyl group are those which do not significantly reduce the anabolic effects or alter the lipolytic effects of the compound. Examples include —OH, halogen (—Br, —Cl, —I and —F), —OR, —O—COR, —CN, —NO$_2$, —COOH, —NH$_2$, —NHR, —NR$_2$, —COOR, —COR, —CHO, —CONH$_2$, —CONHR, —CONR$_2$, —SH, —SR and —NH—C(=NH)—NH$_2$. R is C1–C6 alkyl, benzyl or phenyl.

A substituted non-aromatic heterocyclic ring can also have =O, =S, =NH or =NR where R is as defined above, as a substituent. A substituted aliphatic, substituted aromatic, substituted non-aromatic heterocyclic ring or substituted benzyl group can have one, two or three substituents.

Physiologically acceptable salts of the compounds disclosed herein, including the compounds represented by Structural Formulas (I), (II) and (III) and the compounds shown in Table 1, are also included. Salts can be formed from those compounds which comprise acidic functional groups by reacting with a suitable base. Such salts include those derived from inorganic bases such as ammonium and alkali, and alkaline earth metal hydroxides, carbonates, bicarbonates, and the like, as well as salts derived from basic organic amines such as aliphatic and aromatic amines, aliphatic a diamines, hydroxy alkamines, and the like. Such bases useful in preparing the salts of this invention thus include ammonium hydroxides potassium carbonate, sodium bicarbonate, calcium hydroxide, methylamine, diethylamine, ethylenediamine, cyclohexylamine, ethanolamine and the like.

Because of the amine moiety, salts of the compounds disclosed herein can also be prepared by reacting with a suitable acid. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such physiologically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and like salts. The ammonium chloride, ammonium oxalate, ammonium acetate and the ammonium 4-hydroxybenzoate salts are preferred. Especially preferred are the ammonium acetate and the ammonium 4-hydroxybenzoate salt of Compound 6.

In the structural formulas depicted herein, the bond by which a chemical group or moiety is connected to the remainder of the molecule or compound is indicated by the following symbol:

⸺

For example, the corresponding symbol in Structural Formulas (IV)–(VIII) indicates the bond by which the phenyl ring of the bicyclic ring system is connected to the 3-oxygen atom of the molecule represented by Structural Formula (I), (II) or (III).

The present invention includes solvates of the compounds of Structural Formula I and the physiologically acceptable salts thereof. A particular compound of the present invention or a physiologically acceptable salt thereof may form solvates with water or common organic solvents. Such solvates are included within the scope of compounds of the present invention.

In addition, it will be appreciated that diastereomers exist for the compounds of Structural Formula I and, depending on the substituents, further diastereomers may exist. The compounds of the present invention include mixtures of two or more diastereomers as well as each individual stereoisomer.

It will also be appreciated that some of the heterocycles may exist in tautomeric forms. All such forms are included within the scope of the present invention.

Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (i.e. poultry) such as chickens, ducks, turkeys and geese. Yet other examples of livestock include fish, shellfish and crustaceans raised in aquaculture. Also included are exotic animals used in food production such as alligators, water buffalo and ratites. (e.g., emu, rheas or ostriches). The method of the present invention is preferably used with ruminants, such as cows, heifers, bulls and steers, and with avians, such as chickens, turkeys and ducks.

An "effective amount" of a compound of the present invention is the quantity which, when administered to a livestock animal, increases the quantity of meat and/or quality of meat obtained from the animal.

Increasing the quantity of meat obtained refers to promoting a greater amount of growth in the animal with a treatment compared with the absence of the treatment. Alternatively, increasing the quantity of meat obtained refers to promoting formation of lean body mass. The formation of lean body mass is promoted, for example, when there is a higher ratio of muscle to fat as a result of a treatment than in the absence of the treatment. Alternatively, increasing the quantity of meat obtained refers to improving the efficiency of utilization of food. Food utilization is more efficient when there is a greater body weight gain per a given amount of feed consumed by an animal as a result of a treatment than in its absence.

Increasing the quality of meat refers to an improvement in carcass quality of the animal. Improved carcass quality refers, for example, to the formation of less fatty tissue (subcutaneous fat) and/or greater leanness (improved yield grade), while retaining intramuscular fat (quality graded). Thus, improved carcass quality generally results in meat; that is more healthy to consume, e.g., is less likely to cause elevated triglyceride and/or cholesterol levels, yet retains flavor.

As used herein, a "modestly lipolytic agent" means a compound affording a change in blood non-esterified fatty acid levels of from about 1 to about 500, preferably from about 1 to about 300.

The effective amount to be administered will vary somewhat depending upon the particular animal species being treated and the particular active ingredient employed, but generally will be from about 0.2 to about 1000 parts per, million (ppm: milligrams of compound/kilogram feed) of total daily feed intake. Such amount will provide a dosage of about 0.002 to about 50 mg/kg body weight. A preferred embodiment employs about 0.5 to about 200 ppm, and more preferably from about 1 to about 40 ppm. For example, when practicing the method in animals such as ruminants or swine, the compound will be added to the daily feed ration at about 1 to 100 parts per million of the daily feed ration.

The method of the invention is preferably practiced by orally administering an effective amount of a compound of the present invention to a livestock animal. Other routes of administration can be employed, for instance in ovo, intranasal (e.g., by intranasal misting device) or subcutaneous, intramuscular or intravenous injection; however, such routes are less practical.

For oral administration, a compound of the present invention is preferably admixed with suitable carriers or diluents commonly employed in animal husbandry. Animal feedstuffs comprising a compound of the present invention are provided as a further embodiment of this invention. Typical carriers and diluents commonly employed in such, feedstuffs include corn meal, corncob grits, soybean meal, alfalfa meal, rice hulls, soybean mill run, cottonseed oil meal, bone meal, ground corn, corncob meal, wheat middlings, limestone, dicalcium phosphate, sodium chloride, urea, distillers dried grain, vitamin and/or mineral mixes, cane molasses or other liquid carriers and the like. Such carriers promote a uniform distribution of the active ingredient, and more typically comprise about 20 to about 98 percent by weight of the feedstuff.

While the preferred method for orally administering the compounds of the present invention is via the daily feed rations, the compounds can be incorporated into salt blocks and mineral licks, as well as being added directly to link tank formulations or drinking water for convenient oral consumption. The compounds can additionally be formulated with polymorphous materials, waxes and the like for long-term controlled release, and administered to animals as a bolus or tablet only as needed to maintain the desired daily payout of active ingredient. Compounds can also be administered orally by gavage treatment and/or applied transdermally.

For parenteral administration, the compounds of the present invention can be admixed with conventional carriers such as water, propylene glycol, polyethylene glycols, n-methyl pyrrolidone, glycerol formal, corn oil, sesame oil, calcium stearate, polymeric materials and the like. Such formulations can be molded into pellets and administered as an injection or as a slow-release subcutaneous implant, sustained rumen delivery device or intranasal device. Such administrations can be made as often as needed to ensure the proper dosing of active ingredient to obtain the desired rate of growth promotion and improvement in leanness and feed efficiency.

The compounds of the present invention can be prepared by procedures disclosed in WO 97/10825 to Bell et al., WO 98/09625 to Crowell et al., U.S. Pat. Nos. 5,808,080 and 6,046,227. The entire teachings of these references are incorporated herein by reference. Reaction schemes for preparing these compounds are shown below in Schemes I and II:

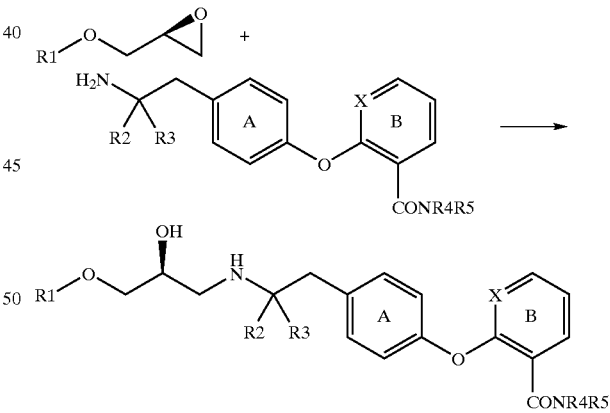

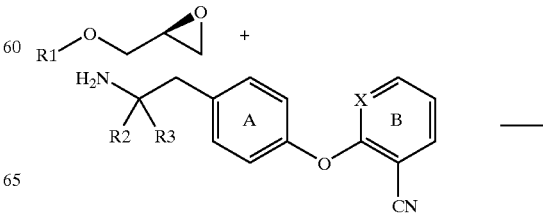

-continued

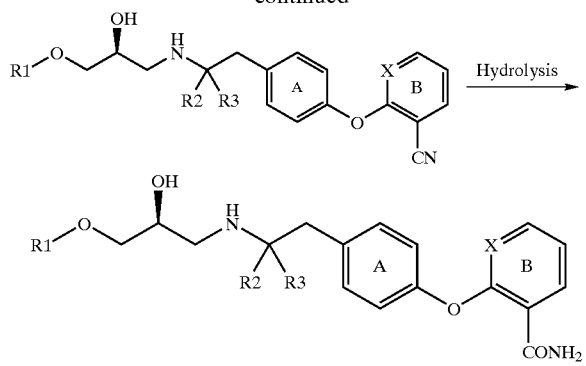

In Schemes I and II, R1–R5, X and Rings A–B are as described above.

The amination of the epoxides in Schemes I and II is carried out under conditions known in the art for this type of reaction. For example, the epoxide may be combined with the amine in an alcohol, preferably, ethanol at room temperature to the reflux temperature of the reaction mixture. For example, the reaction is carried out under conditions generally described in Atkins et al., *Tetrahedron Letters* 27:2451 (1986) the entire teachings of which are incorporated herein by reference. An example of specific conditions for reacting an epoxide with an amine is provided in Example 5.

The hydrolysis reaction shown in Scheme II can be carried out according to methods known in the art using, for example, polyphosphoric acid, $H_2O_2$ and $K_2CO_3$ in dimethylsulfoxide, $H_2O_2$ and ammonium hydroxide, $H_2O_2$ and sodium hydroxide, potassium hydroxide and t-butanol, or water and HCl. An example of specific conditions for hydrolyzing a nitrile is provided in Example 6.

A preferred method of preparing Compound 6 in Table 1 comprises aminating an epoxide represented by the following structural formula

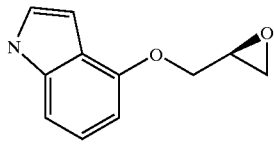

with an amine represented by the following structural formula

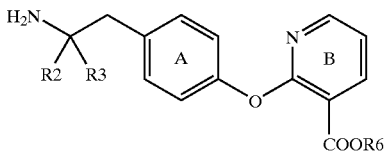

wherein R6 is methyl or ethyl, then amidating the COOR6 group with ammonia to form Compound 6. Examples of specific conditions for synthesizing Compound 6 according to this, process are provided in Examples 13–15.

Substituents which interfere with the reactions shown in Schemes (I) and (II) can be present, provided that they are first converted to a protected form. Suitable protecting groups are known to those skilled in the art and are disclosed in Green and Wuts, "*Protecting Groups in Organic Synthesis*", John Wiley and Sons, 1991, the teachings of which are incorporated herein by reference.

The individual optically active isomers of the compounds of the present invention may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., Enantiomers, Racemates; and Resolutions, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The invention is illustrated by the following examples, which are not meant to be limiting in any way.

EXEMPLIFICATION

Example 1

Preparation of 4-[(2S)-Oxiranylmethoxy]-1H-indole

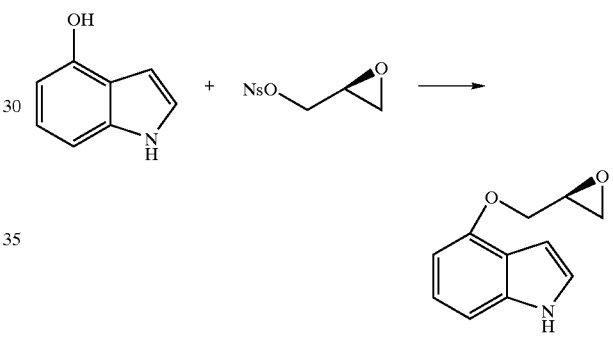

Powdered $K_2CO_3$ (40 grams, 289 mmol, 300 mesh) was added to dimethyl sulfoxide (DMSO) (200 mL) containing $H_2O$ (4 mL) under $N_2$ at room temperature and the mixture was stirred for 30 minutes. 4-Hydroxyindole (25.2 grams, 189 mmol) was added to the mixture (slight exotherm to 27° C.) and the mixture was stirred for 10 minutes. (S)-Glycidyl nosylate (50.0 grams, 193 mmol, 98.5% ee) was added (slight endotherm). The slurry was stirred for 30 minutes at 20–25° C. and for 23 hours at 25–27° C. until the reaction was complete. The mixture was diluted with acetone (400 mL) and filtered. The cake was washed with acetone (400 mL) and the combined filtrates were concentrated to a volume of ca. 250 mL under vacuum while maintaining the temperature below 35° C. This concentrate was added dropwise, over ca. 2 hours, to deionized $H_2O$ (650 mL) held at a temperature of 15–20° C. with an ice/water bath. The product slurry was stirred for 1 hour at this temperature and for 30 minutes at 5–10° C. The solid was isolated by filtration and washed with cold deionized $H_2O$ (150 mL). The solid was dried under vacuum at 35° C. to yield 30.3 grams of product.

Silica Gel 62 (1.6 grams, 0.05% wt/wt) was added to a solution of the crude product above (30.3 grams, 171 mmol) in $CH_2Cl_2$ (100 mL) at room temperature and the slurry was stirred for 1 hour under $N_2$. The mixture was then vacuum filtered and the cake was rinsed with $CH_2Cl_2$ (20 mL). Heptane (500 mL) was added dropwise to the filtrate over 1 hour at room temperature to precipitate the product. The resulting slurry was stirred for 30 minutes at room temperature and for 30 minutes at 0–5° C. The mixture was filtered, rinsed with cold heptane (150 mL), and vacuum-dried at 35° C./5 Torr to give 26.5 grams of product (79%, yield), mp 72.4–74.0° C., which then solidifies and remelts at 79.8–81.3° C.

Example 2
Preparation of 4-(2-Methyl-2-Nitropropyl)Phenol

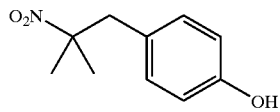

Potassium tert-butoxide (29.6 grams, 264 mmol) was added to a solution of 2-nitropropane (260 mL, 2.90 mol), 4-hydroxybenzyl alcohol (65.0 grams, 524 mmol) in diglyme (260 mL) at room temperature with mechanical stirring. During the addition the reaction temperature increased from 25° C. to 39° C. The reaction mixture was heated to reflux and stirred for 6 hours at ca. 137° C., using a Dean-Stark trap to remove the water as it was formed (total volume of distillate 28 mL, 7 mL aqueous phase). After cooling to room temperature, deionized $H_2O$ (325 mL) and ethyl acetate (520 mL) were added to the reaction solution. The phases were separated and the organic phase was washed with deionized $H_2O$ (2×325 mL) The organic phase was concentrated by rotary evaporation at 78° C. to give 181.2 grams of an oil. This oil was dissolved in methanol (65 mL) for use in the next reaction. The concentration of the resulting solution was determined by $^1H$ NMR analysis to be 56.3% by weight (99.6% yield).

Example 3
Preparation of the Acetate Salt of 4-(2-Amino-2-Methylpropyl)phenol

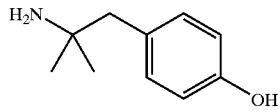

To a $N_2$-degassed solution of 4-(2-methyl-2-nitropropyl) phenol (45.0 grams, 230 mmol) in MeOH (450 mL) was added 5% Pd/C (13.5 grams of 50% water-wet catalyst, 15% by weight on a dry-basis). The mixture was pressurized to 35–40 psi with hydrogen and heated to 60° C. with vigorous agitation. When the reaction was complete (ca. 6 hours), the mixture was cooled to room temperature and the catalyst was carefully removed by filtration through Hy-Flow filter aid. The cake was washed with 50° C. methanol (135 mL) and the, combined filtrates were concentrated by rotary evaporation to a net weight of ca. 120 grams. The concentrate was diluted with ethyl acetate (500 mL), and a solution of acetic acid (14.2 grams, 235 mmol) in ethyl acetate (250 mL) was added to the resulting solution over 30 minutes. The resulting slurry was stirred for 2 hours at room temperature. The slurry was filtered and the solid was washed with ethyl acetate (2×100 mL). The product was vacuum-dried at 65° C./5 Torr for 24 hours to give 46.5 grams (89.6%) of a white crystalline solid, mp 209–215.9 (dec).

Example 4
Preparation of 2-[4-(2-Amino-2-Methylpropyl)phenoxy]-3-carbonitrilepyridine

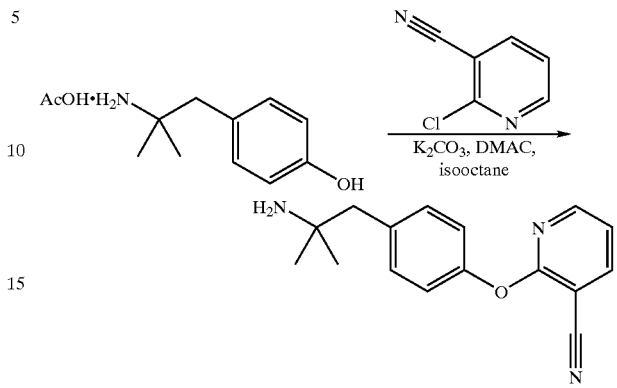

Into a 3 L three-necked flask fitted with a mechanical stirrer, Dean-Stark trap with condenser, and a thermocouple was placed the acetate salt of 4-(2-amino-2-methylpropyl) phenol (50.78 g, 0.23 mol), 2-chloronicotinonitrile (32.8 g, 0.24 mol) and powdered $K_2CO_3$ (77.7 g, 0.56 mol). To the solids were added N,N-dimethylacetimide (609 mL) and isooctane (2,2,4-trimethylpentane, 122 mL). The Dean-Stark trap was charged with isooctane, and the system was purged with $N_2$. The system was then heated to reflux with vigorous stirring and allowed to reflux for 1 hour. The olive green reaction mixture was then cooled to 30° C. over one hour, and the mixture filtered through paper. The filter cake was washed with DMAC (250 mL) and the filtrate stripped at 80° C. for 1.5 hours under house vacuum to yield a thick, dark green oil. The oil was taken up in dichloromethane (580 mL) and washed with deionized water (1160 mL). The layers were separated and the organic layer washed with more water (250 mL). The organic layer was then mixed with water (1 L) and the pH was adjusted to approx. 1 with 25 mL of concentrated HCl. The layers were separated and the aqueous/product layer washed with dichloromethane (250 mL). The aqueous phase was then mixed with dichloromethane (1 L) and the pH adjusted to 12–13 with 5N NaOH. The layers were separated and the organic layer dried over $Na_2SO_4$, filtered, and stripped to yield solid brown product (53 g, 88%, >99% by HPLC: SB-C18 column, 40/60 isocratic mixture of acetonitrile, 0.1% TFA in water, retention time of product is 3.3 minutes).

A 20 gram portion was recrystallized from toluene (60 mL) and heptane (200 mL) to provide a sample for analytical characterization, mp 91.0–94.5° C. Anal. Calcd for $C_{16}H_{17}N_3O$: C, 71.89; H, 6.41; N, 15.72. Found: C, 71.20; H, 6.38; N, 15.61.

Example 5
Preparation of (S)-2-[4-[2-[2-Hydroxy-3-(1H-indol-4-yloxy)propylamino]-2-methylpropyl]-phenoxy]-3-pyridinecarbonitrile, hydrochloride salt

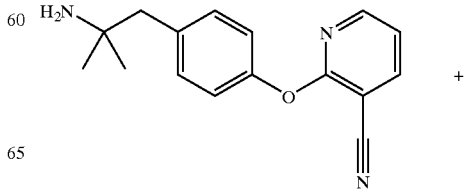

-continued

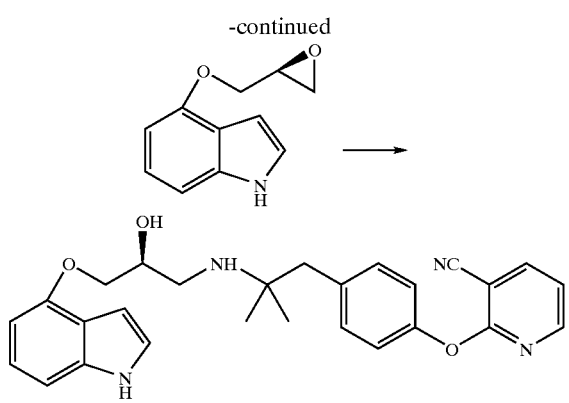

Into a three-necked round-bottom flask fitted with a condenser, nitrogen inlet, mechanical stirrer, and a thermocouple was placed 4-[(2S)-oxiranylmethoxy]-1H-indole (8.5 grams, 44.9 mmol, 98.5% ee), 2-[4-(2-amino-2-methylpropyl)phenoxy]-3-carbonitrilepyridine (21.01 grams, 78.6 mmol) and isopropyl alcohol (255 mL). The reaction was heated at reflux (78° C.) for 17 hours under $N_2$. The solution was then allowed to cool to room temperature and stirred for one hour. The cooled mixture was filtered through a Hy-Flo filtering aid (16.5 grams) and the filter cake was washed with isopropanol (43 mL). The filtrate was concentrated to a net weight of 55 grams under full vacuum at 50° C. To the concentrated solution was added ethyl acetate (85 mL) and the resultant solution was concentrated under the same conditions to a net weight of 52 grams. The concentrate was then taken up in ethyl acetate (230 mL), and 2.5% wt/vol NaCl solution (150 mL) was added. The biphasic system was vigorously stirred and the pH was adjusted to 7.2 with glacial acetic acid. The phases were separated and the organic phase was extracted with 2.5% brine (2×50 mL). The organic phase was washed sequentially with NaOH/NaCl solution (50 mL, 0.89 grams NaOH), and water (50 mL).

Salt formation:

The organic phase was concentrated to 40 grams net weight under the conditions noted above. The concentrate was diluted with ethyl acetate and stripped to 44.9 grams to dry the solution azeotropically. The solution was then divided into three equal portions and one third of the solution was concentrated to 14 grams (about 6.83 grams of freebase). To the concentrate was added adequate volumes of ethyl acetate (40 mL) and ethanol (18.7 mL) to bring the solution to a ratio of 1/3.5 ethanol to ethyl acetate, taking into account residual solvent in the product concentrate, and a dilution factor of 12.3 mL/gram of product. The solution was brought to reflux and the pH was adjusted to 3.5 with a 0.5 N solution of HCl in ethyl acetate (about 30.7 mL). The solution should now have a ratio of approximately 1/4.3 ethanol to ethyl acetate with a dilution factor of approximately 14.5 mL/gram of product. The solution was allowed to cool to room temperature and was stirred for 15 hours, at which time the solution was cooled in an ice bath and was stirred at 0° C. for 3 hours. The slurry was then filtered, and the crystals were washed with cold 1:4 ethanol/ethyl acetate (10 mL). The product was dried over night under vacuum at 50° C. to give 5.5 grams (75%) of a white crystalline solid, mp 188.8–191.0° C. Anal. Calcd for $C_{27}H_{29}ClN_4O_3$: C, 65.78; H, 5.93; Cl, 7.19; N, 111.36. Found: C, 65.59; H, 6.12; Cl, 7.25; N, 11.36.

The acidic aqueous extract from the workup above was adjusted to pH 12–13 with 1 N NaOH solution in a vigorously stirred biphasic system with MTBE (80 mL). The layers were separated, and the organic extract was dried over $Na_2SO_4$, filtered, and concentrated to a solid in 80–90% yield.

Example 6

Preparation of the free base of Compound 6 From (S)-2-[4-[2-[2-Hydroxy-3-(1H-indol-4-yloxy)propylamino]-2-methylpropyl]-phenoxy]-3-pyridinecarbonitrile, hydrochloride salt

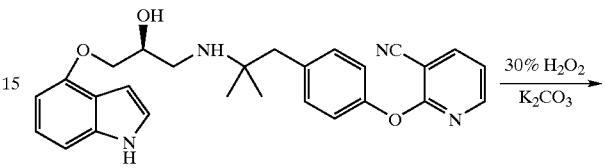

Compound 6

Into a three-necked, round-bottom flask fitted with a nitrogen inlet, mechanical stirrer, and a thermocouple were placed (S)-2-[4-[2-[[2-hydroxy-3-(1H-indol-4-yloxy)propyl]amino]-2-methylpropyl]phenoxy]-3-pyridinecarbonitrile, hydrochloride salt (10 grams, 20.3 mmol), and DMSO (70 mL). The reaction was stirred at room temperature for 30 minutes to assure complete dissolution. The solution was placed in a cooling water bath and 2.2 N NaOH (10 mL, 22 mmol) was added over 10 minutes while maintaining the temperature below 35° C. After stirring for 30 minutes, 30% aqueous $H_2O_2$ (2.71 m) was added in seven equal portions over 40 minutes while maintaining the temperature below 35° C. The reaction was complete after 30 minutes. An aqueous solution of $Na_2SO_3$ (1.60 grams, 12.7 mmol in 35 mL of water) was added to the reaction mixture in 4 portions over 15 minutes while maintaining the reaction temperature below 35° C. After 15 minutes the thick solution tested negative for peroxide. Ethyl acetate (75 mL) was added and the solution was stirred for 30 minutes. Additional ethyl acetate (100 mL) and $H_2O$ (100 mL) were added and the phases were separated. The organic phase was washed with $H_2O$ (100 mL). The combined aqueous fractions were back extracted with ethyl acetate (100 mL) and the organic phase was combined with the earlier organic fractions. A portion of the solution (10%) was saved as a retainer of the crude freebase of Compound 6, which was obtained by removal of the solvent. Compound 6 was analyzed by electro spray ionization mass spectrometry; the molecular ion peak was 475.0 (calculated molecular weight was 474.56)

The remainder of the combined organic extracts was concentrated by rotary evaporation at 50° C. to a net weight of 18–20 grams. The residue was dissolved in ethyl acetate and ethanol to give a 7:1 ratio of ethyl acetate/ethanol, with a concentration of 8 mL/grams of freebase. The percent water was determined by Karl Fischer titration. The water content should be between 1.0–2.0% w/w for maximum yields in the crystallization. After the solution was heated to reflux, glacial acetic acid (1.10 grams, 18.3 mmol) was added and the solution was seeded. The slurry was cooled to room temperature and stirred overnight. After cooling at 0° C. for 2 hours, the product was filtered, the cake was washed with cold 7:1 ethyl acetate/ethanol (20 mL), and the solid was air-dried for 1 hour. The product was vacuum-dried overnight at 70° C. to give 7.4 grams (96% purity, 86% yield) of product as a white crystalline solid, mp 137

(shrinks) 143.1–153.2° C. Anal. Calcd for C$_{27}$H$_{30}$N$_4$O$_4$.C$_2$H$_4$O$_2$: C, 65.15; H, 6.41; N, 10.48. Found: C, 65.55; H, 6.37; N, 10.88.

Example 7
Preparation of Salts of Compound 6

Hydrochloride Salt

A solution of HCl in ethanol (7.04 mL of a 0.6 M solution, 4.22 mmol) was added to a refluxing solution of the Compound 6 freebase (2.0 grams, 4.2 mmol) in ethanol, (9.0 mL). The pH was carefully adjusted to 3.0, adding triethylamine or HCl as required. The solution was seeded and allowed to cool to room temperature, at which point it was stirred overnight. The slurry was cooled to 0° C. for 2 hours, filtered, and the filtrate washed with 3 mL of cold ethanol. The off-white solid was vacuum dried overnight at 50° C./5 Torr to give 1.90 grams (88% yield) of an off-white solid, mp 207.0–211.0° C. Anal. Calcd for C$_{27}$H$_{30}$N$_4$O$_4$.HCl: C, 63.46; H, 6.11; N, 10.96. Found: C, 63.00; H, 6.19; N, 11.04.

Acetate Salt

Acetic acid (278 mg, 4.6 mmol) in ethanol (2.0 mL) was added to a refluxing solution of the Compound 6 freebase; (2.0 grams, 4.2 mmol) in ethyl acetate (14.0 mL). The solution was seeded and cooled slowly to room temperature and stirred overnight. The slurry was cooled at 0° C. for 2 hours, filtered, and washed with cold 7:1 ethyl acetate/ethanol (4 mL). The white solid was vacuum dried overnight at 70° C./5 Torr to give 1.94 grams (86% yield) of an off-white solid, mp 148.7–154.2° C. Anal. Calcd for C$_{27}$H$_{30}$N$_4$O$_4$.C$_2$H$_4$O$_2$: C, 65.15; H, 6.41; N, 10.48. Found: C, 65.72; H, 6.30; N, 11.06.

Analysis by X-ray powder diffraction of other lots prepared by a similar process were shown to be crystalline solids.

The 4-Hydroxybenzoate Salt

A solution of 4-hydroxybenzoic acid (12.53 grams, 90.7 mmol) in hot ethanol (171 mL) was added to a refluxing solution of freebase (42.8 grams, 90.2 mmol) in ethyl acetate (343 mL) and the resulting solution refluxed for 15 minutes. The solution was decanted away from a small amount of insoluble residue and seeded. The solution was cooled slowly to room temperature and was stirred overnight. The slurry was cooled to 0° C. for 2 hours. The solids were filtered, washed with cold 2:1 ethyl acetate/ethanol, and vacuum dried overnight at 70° C./5 Torr to give 45.4 grams (82% yield) of an off-white solid, mp 148.3–150.5, which then solidifies and remelts at 159–186.9° C. (dec). Both the wet cake and the dried solid were shown to be crystalline by X-ray powder diffraction.

Oxalate Salt

A hot solution of oxalic acid (37.8 mg, 0.42 mmol) in methanol (2.5 mL) was added to a refluxing solution of freebase (250 mg, 0.53 mmol) in methanol (2.5 mL). The solution was heated at reflux for 1 hours. The solution was cooled slowly to room temperature and stirred overnight. The slurry was cooled to 0° C. for 2 hours. The solids were filtered, washed with cold methanol, and dried overnight at 70° C./5 Torr to give 194 mg (65%) of an off-white solid, mp 214.9 (dec). Both the wet cake and the dried solid were shown to be crystalline by X-ray powder diffraction.

Example 8
Synthesis of 2-[4-(2-amino-2-methylpropyl)phenoxy]-3-pyridinecarboxylic acid, ethyl ester.

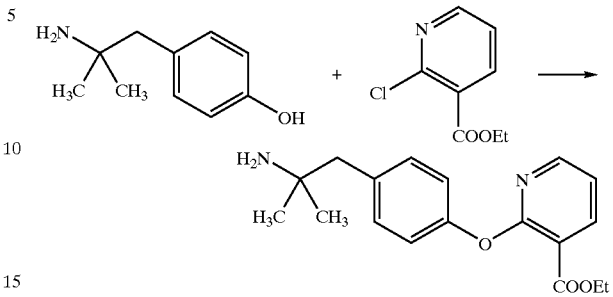

4-(2-Amino-2-methylpropyl)phenol (55.18 grams, 244.9 mmol) was added to 5.05 N KOH (97.2 mmol, 2.0 equiv). The mixture was warmed to 50° C. to give a homogeneous yellow solution. Chlorobenzene (1104 mL) and N,N-dimethylacetamide (10.7 grams, 122 mmol) were added and the mixture was heated to reflux (ca. 100° C.). The water was removed azeotropically via a Dean-Stark trap. At ca. 125° C. a solid began to form. When the pot temperature reached 132° C. the water had been removed and the reaction mixture was a thick but stirrable slurry (mechanical stirring required). The Dean-Stark trap was removed and an additional 100 mL of chlorobenzene was removed and discarded. Dry chlorobenzene (50 mL) was added to the slurry, followed by ethyl 2-chloronicotinate (50.0 grams, 269 mmol) in chlorobenzene (50 mL). The slurry was heated at reflux until the reaction was complete (ca. 24, hours). As the reaction progressed the slurry thinned and became beige in color. After cooling to room temperature, water (385 mL) and 1 N NaOH (25 mL, 0.1 equiv) were added to the mixture and the phases were separated. The organic phase was washed with water (285 mL) and the solution was concentrated to a net weight of 700 grams (9.83% potency by HPLC, 89% yield) for use in the next reaction.

Example 9
Preparation of 2-[4-(2-amino-2-methylpropyl)phenoxy]-3-pyridinecarboxylic acid, ethyl ester, acetic acid salt.

Ethyl 2-[4-(2-amino-2-methylpropyl)phenoxy]-3-pyridinecarboxylate (10.3 grams, 32.8 mmol) was dissolved in ethyl acetate (52 mL) and heptane (41 mL) and the solution was heated to reflux. Acetic acid (1.97 grams, 38.8 mmol) was added, the solution was seeded, and cooled slowly to room temperature. After 30 minutes at room temperature, the slurry was cooled to 0° C. and stirred for 1.5 hours. The product was filtered, washed with cold 1:1 ethyl acetate/heptane (20 mL), and vacuum-dried at 50° C. for 18 hours to give 10.29 g (97% purity, 81% yield), mp 122.9–124.5° C.

Example 10
Preparation of (S)-2-[4-[2-[2-Hydroxy-3-(1H-indol-4-yloxy)propylamino]-2-methylpropyl]-phenoxy]-3-pyridinecarboxylic acid, ethyl ester, 4-hydroxybenzoic acid salt 4-[(2S)-Oxiranylmethoxy]-1H-indole (9.00 grams, 47.6 mmol) was added to a solution of ethyl 2-[4-(2-amino-2-methylpropyl)-phenoxy]-3-pyridinecarboxylate (162.8 grams of a 10.1% w/w solution in chlorobenzene, 52.3 mmol) and the resulting solution was heated at reflux for 37 hours. When the epoxide had been consumed, the solution was cooled to 80° C., and a 50° C. solution of 4-hydroxybenzoic acid (6.57 grams, 47.6 mmol) in 2B-3 ethanol (34 grams) was added in one portion. The homogeneous solution was seeded at 70° C. and cooled slowly to room temperature with stirring. After stirring for 1 hour at 0° C. the slurry was filtered, washed with chlorobenzene (3×50 mL), and vacuum-dried at 70° C. for 18 hours to give 20.82 grams (68% yield) of product as an off-white solid, mp 172.4–175° C. Anal. Calcd for $C_{29}H_{33}N_3O_5 \cdot C_7H_6O_3$: C, 67.38; H, 6.12; N, 6.54. Found: C, 67.18; H, 6.07; N, 6.77.

Example 11
Preparation of (S)-2-[4-[2-[2-Hydroxy-3-(1H-indol-4-yloxy)propylamino]-2-methylpropyl]-phenoxy]-3-pyridinecarboxylic acid, ethyl ester The 4-hydroxybenzoic acid salt of the title compound (17.1 grams, 26.6 mmol) was added with stirring to a mixture of methyl tert-butyl ether (200 mL, MTBE) and 1 N NaOH (75 mL). When all of the initial solid was dissolved a small amount of a dark green solid remained which was easily removed by filtration (Whatman #1 paper). The organic phase was washed with brine (2×30 mL) and dried over anhydrous MgSO$_4$. The drying agent was removed by filtration. The MTBE solvent was exchanged with methanol by concentrating the solution using rotary evaporation, redissolving the residue in MeOH, and reconcentrating again. This process was repeated and the residue was dissolved in anhydrous methanol and used directly in the subsequent reactions.

Example 12
Preparation of (S)-2-[4-[2-[2-Hydroxy-3-(1H-indol-4-yloxy)propylamino]-2-methylpropyl]-phenoxy]-3-pyridinecarboxamide, acetic acid salt

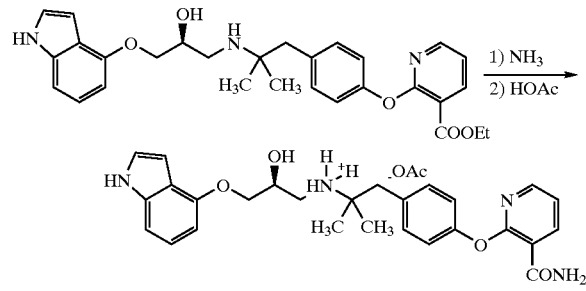

A solution of ethyl (S)-2-[4-[2-[2-hydroxy-3-(1H-indol-4-yloxy)propylamino]-2-methylpropyl]-phenoxy]-3-pyridinecarboxylate (13.2 grams, 26.1 mmol) in methanol (66 mL) was poured into a vessel that was then pressurized and vented 3 times with 25 pounds per square inch gauge (psig) ammonia. The internal vessel pressure was then brought to 50 psig with ammonia and the yellow solution stirred at 24° C. for 19 hours. The solvent and ammonia were removed by rotary evaporation until 25 grams remained in the flask. Ethanol (100 mL, 2B-3) was added and the solvent again removed by rotary evaporation until 26 grams remained. This addition of ethanol and evaporation was repeated 3 more times for the solvent exchange into ethanol and removal of ammonia. After the last evaporation, the contents of the flask weighed 25.0 grams and was taken to be the theoretical 12.5 g of freebase and 12.5 grams of ethanol. Ethyl acetate (87.7 mL) and H$_2$O (1.0 mL) were added and the solution was brought to reflux. Acetic acid (1.73 grams, 28.8 mmol) was added and the solution was seeded. After 1 hour, heating was removed from the white mixture. After stirring at 24° C. for 1 hour, the white solid was collected by vacuum-filtration and washed twice with 7:1, ethyl acetate:ethanol (20 mL) and once with with 7:1 ethyl acetate:ethanol (10 mL). Vacuum drying overnight at 50° C./5 Torr gave 11.6 g (96.9% purity, 97% yield) as a white solid, mp 157–158° C. Anal. Calcd for $C_{27}H_{30}N_4O_4$: C, 65.15; H, 6.41; N, 10.48. Found: C, 65.01; H, 6.28; N, 10.26.

Example 13
Preparation of (S)-2-[4-[2-[2-Hydroxy-3-(1H-indol-4-yloxy)propylamino]-2-methylpropyl]-phenoxy]-3-pyridinecarboxylic acid, ethyl ester, 4-hydroxybenzoic acid salt 4-[(2S)-Oxiranylmethoxy]-1H-indole (8.00 grams, 42.3 mmol was added to ethyl 2-[4-(2-amino-2-methylpropyl)-phenoxy]-3-pyridinecarboxylate (14.4 grams, 46.5 mmol) in 2B-3 ethanol (80 mL) and the resulting solution was heated at reflux for 20 hours until the epoxide had been consumed. The solution was cooled to 70–75° C., and a 70–75° C. solution of 4-hydroxybenzoic acid (5.9 grams, 42.3 mmol) in 2B-3 ethanol (20 mL) was added in one portion. The homogeneous solution was seeded and stirring continued at 70–75° C. for 1 hour. The mixture was cooled to 26° C. and stirred for 1 hour, then cooled to 5° C. and stirred for an additional hour. The solid was collected by filtration, washed with 2B-3 ethanol (45 mL), and vacuum-dried at 50° C. for 45 hours to give 21.8 grams (80.4% yield) of product as an off-white solid, mp 174–176° C.

Example 14
Preparation of (S)-2-[4-[2-[2-Hydroxy-3-(1H7 indol-4-yloxy)propylamino]-2-methylpropyl]-phenoxy]-3-pyridinecarboxylic acid, ethyl ester To the 4-hydroxybenzoic acid salt of the title compound (40.0 grams, 62.3 mmol) were added with stirring methyl tert-butyl ether (350 mL, MTBE) and methyl alcohol (20 mL). Stirring was continued for 90 minutes until the solid was well dispersed, then 1N sodium hydroxide (160 mL) and deionized water (40 mL) were added. Once the solid was dissolved the layers were separated, and the organic phase was extracted twice with a solution of deionized water (120 mL) and sodium chloride (8.0 g). After cooling to 0–5° C. and filtering through glass paper the organic layer was concentrated to 80 mL at 40° C. and 24–28 inches Hg. Methyl alcohol (160 mL) was added and the volume again reduced to 80 mL. The total volume was brought back to 240 mL with methyl alcohol and this solution was used directly in the subsequent reactions.

Example 15
Preparation of (S)-2-[4-[2-[2-Hydroxy-3-(1H-indol-4-yloxy)propylamino]-2-methylpropyl]-phenoxy]-3-pyridinecarboxamide, acetic acid salt A solution of ethyl (S)-2-[4-[2-[2-hydroxy-3-(1H-indol-4-yloxy)propylamino]-2-methylpropyl]-phenoxy]-3-pyridinecarboxylate (31.4 grams, 62.3 mmol) in methyl alcohol (264 mL) was pressurized and vented 3 times with 5 psig ammonia. The internal vessel pressure was then brought to 5 psig with ammonia and the yellow solution stirred at 40° C. for 22 hours. The volume was concentrated to 60 mL art 30–40° C. and 25 inches Hg. Methyl ethyl ketone (450 mL, MEK) was added and the volume reduced to 60 mL at 40–50° C. and 25 inches Hg. MEK was again added (200 mL) and the volume reduced to 60 mL. At 15–20° C. the contents were brought back to a total volume 300 mL using MEK, filtered using a 20 micron fritted glass filter funnel, then rinsed with MEK to give a total filtrate volume of 310 mL. The solution was heated to 65° C. and a solution of glacial acetic acid (3.75 g, 62.4 mmol) in MEK (15 mL) at 65° C. was added. After seeding the mixture was stirred at 65° C. for 90 minutes, then allowed to cool to 25° C. with stirring over 14 hours. The mixture was cooled to 3° C. and stirred for 1 hour. The slurry was collected by filtration, washed with MEK (90 mL), and vacuum-dried at 70° C. for 46 hours to give 30.3 grams (90.9% yield) of product as an off-white solid, mp 156–158° C.

Example 16

Preparation of 4-Hydroxyindazole and other R1—OH Compounds

4-Hydroxyindazole may be prepared according to procedures disclosed in Davies, *J. Chem. Soc.* 1955:2412 (1955) and H. D. Porter and W. D. Peterson, "Organic Synthesis", Collective Volume III, p.660. The entire teachings of these references are incorporated herein by reference. Specific conditions for preparing 4-hydroxyindazole are provided below.

A. Preparation of 4-Nitroindazole from 2-Methyl-3-Nitroaniline

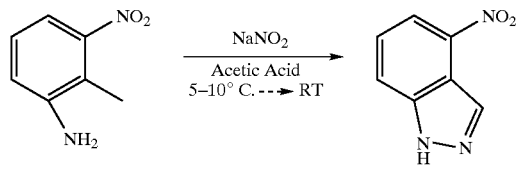

Sodium nitrite (20 grams, 0.29 mol) was dissolved in 50 mL water. This solution was added all at once to 2-methyl-3-nitroaniline (20 grams, 0.13 moles) in glacial acetic acid near zero degrees C. The reaction was stirred vigorously with an overhead stirrer. An immediate precipitate occurred upon addition of sodium nitrite solution. The reaction was allowed to reach room temperature and stirred overnight. The precipitate was filtered off and the filtrate was concentrated in vacuo. The dark orange solid was suspended in water, filtered, and dried yielding 14–21 grams dark orange solid (99% yield).

B. Preparation of 4-Aminoindazole From 4-Nitroindazole

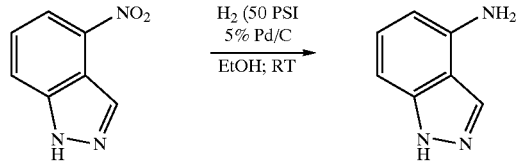

4-Nitroindazole (12 grams) was dissolved in ethanol (300 mL) with warming in a Parr hydrogenated vessel. 5% palladium on carbon (12 grams) was added to the vessel. The reaction was pressurized to 50 PSI and shaken for 1 hours TLC indicated product formation and loss of starting material. The reaction mixture was filtered over Celite. The catalyst was thoroughly washed with methanol until all product was flushed off. The filtrate was concentrated to a dark gray solid, which was dissolved in ethyl acetate and filtered over a silica pad. The filtrate was concentrated to a brownish solid (9.6 grams, 97% yield).

C. Preparation of 4-Hydroxyindazole From 4-Aminoindazole

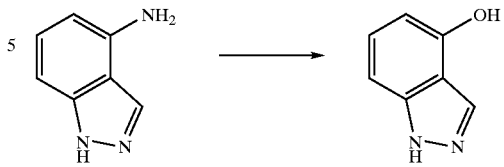

4-Aminoindazole (9.6 grams, 0.072 moles) was dissolved into a glass reaction vessel containing 7.2 grams of concentrated sulfuric acid in 75 mL water. This was sealed into a stainless steel autoclave and heated to 170 degrees C. overnight. The reaction mixture contained much black precipitate. The reaction mixture was diluted with ethyl acetate and water into a separatory funnel and partitioned. The aqueous layer was extracted several times with ethyl acetate until all the product was out of the aqueous fraction. The combined organic fractions were washed with brine, dried with magnesium sulfate, filtered, and concentrated to a dark brown or black oil. The product was purified by passing it over a silica pad with 50% ethyl acetate/hexane mixture resulting in an off-white solid (3.3 grams, 33% yield).

By utilizing the general procedures described herein, those skilled in the art may similarly prepare other R1—OH aryloxy compounds and salts thereof, such as Compounds 2, 4 and 8–13 of the present invention (See, Example 17, Table 1).

Compounds 2, 4 and 8 were prepared by the techniques described above and analyzed by electro spray ionization mass spectrometry. The molecular ion peak for Compound 2 was 476.0 (calculated molecular weight 475.55); Compound 4 was 508.0 (calculated molecular weight 507.61); and Compound 8 was 492.24 (calculated molecular weight 492.01).

Example 17

Intravenous Administration of the Compounds of the Present Invention to Cattle

Intravenous administration of the compounds of the present invention to cattle increases serum non-esterified fatty acids and decreases serum urea. In this Example, angus/angus cross calves, both heifers and steers, weighing approximately 282 pounds (128 kg) initially to 788 pounds (357.8 kg) over the course of these studies, were placed in pens at 5 calves per pen. The cattle were acclimated to the pens for at least 1 week prior to initiating the study.

Calves were fed ad libitum twice daily, (approximately 6–15 pounds (2.7–6.8 kg)/day). During the treatment day, in the A.M. period, the feeding times were staggered to ensure that all animals were fed approximately one hour before the treatments were administered. During the P.M. treatment period, the cattle were fed immediately after receiving the P.M. injection.

After taking a pretreatment (T=0) blood sample from each animal, a 40 μg per kilogram dose of a test compound was administered intravenously in the jugular vein at 6:30 A.M. and 2:30 P.M. Each test compound was administered at a concentration of 1.00–1.25 mg/ml in a treatment vehicle that was a 50/50 mixture of polyethylene glycol 200/water.

A blood sample was taken at fifteen minutes post-treatment (T+15 min). The calves were returned to their respective pens until their next treatment, approximately eight hours later. The next morning at 6:30 A.M. a blood sample was collected from all calves at 24 hours post-treatment (T+24 h). All blood samples were analyzed for the non-esterified fatty acid level (NEFA) and serum urea nitrogen level (SUN). The post-treatment NEFA and SUN levels in each individual animal were compared with the levels found before treatment. The results are shown in Table 1.

TABLE 1
| STRUCTURE | ΔNEFA* 15 Min. | ΔNEFA** 24 Hours | Δ% SUN*** 24 Hours |
|---|---|---|---|
| Vehicle only | ~0 | ~0 | ~0 |
| 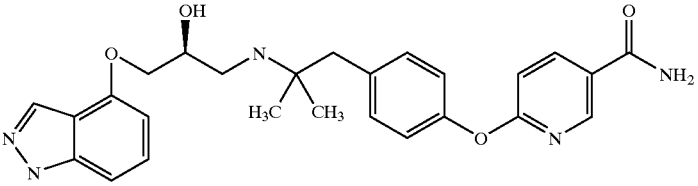 Compound 1 | 554.4 | 820.9 | −28.7 |
| 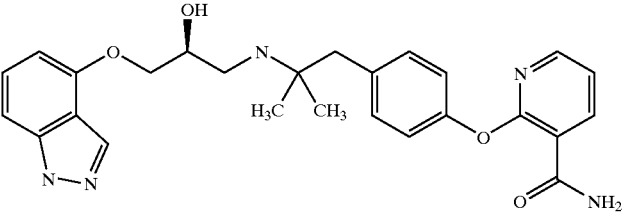 Compound 2 | 141.2 | 742.4 | −39.3 |
| 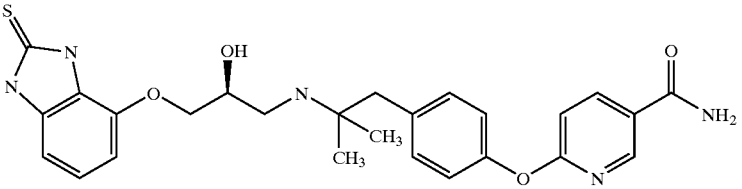 Compound 3 | 379.4 | 200.2 | −38.2 |
| 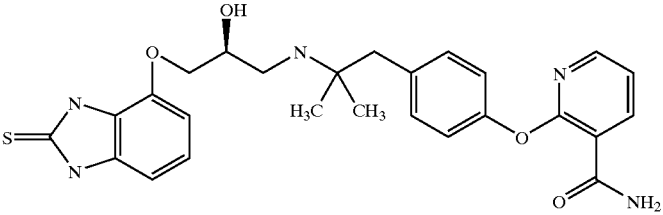 Compound 4 | 283.1 | 265.3 | −57 |
| 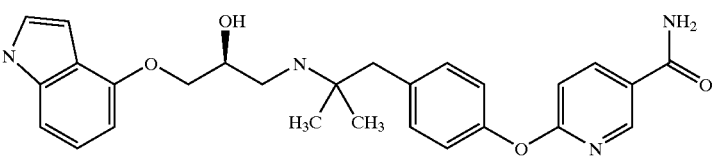 Compound 5 | 170.8 | −5.6 | −28.6 |
| 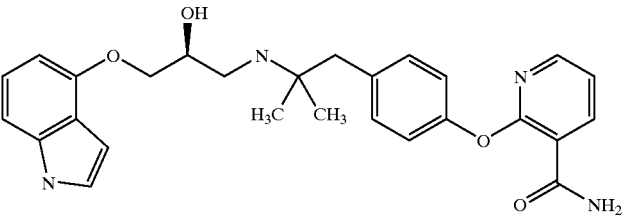 Compound 6 | 40.7 | −1.44 | −47 |

TABLE 1-continued

| STRUCTURE | ΔNEFA*<br>15 Min. | ΔNEFA<br>24 Hours | Δ% SUN*<br>24 Hours |
|---|---|---|---|
| 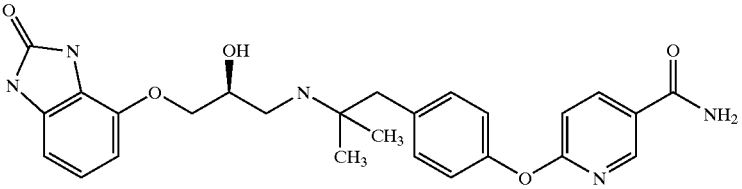<br>Compound 7 | 134.1 | −4.2 | −9.7 |
| 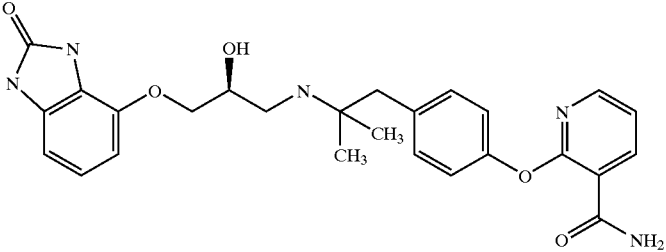<br>Compound 8 | 321.4 | 35.6 | −14.2 |

*The increase in NEFA (μmol/liter) in the blood of animals treated with the indicated test compound compared with baseline (T = 0) NEFA value for each individual at 15 minutes post treatment (ΔNEFA = T + 15 min NEFA value − T = 0 NEFA value). Values presented are the mean of five animals.
**The increase in NEFA (μmol/liter) in the blood of animals treated with the indicated test compound compared with baseline (T = 0) NEFA value for each individual 24 hours post treatment (ΔNEFA = T + 24 h NEFA value − T = 0 NEFA value). Values presented are the mean of five animals.
***The percent decrease in SUN in the blood of animals treated with the indicated test compound at 24 hours post treatment compared with the baseline (T = 0) SUN value for each individual. Values presented are the mean of five animals.

$$\% \, \Delta\text{SUN} = \frac{(T + 24 \, h \, \text{SUN}) - (T = 0 \, \text{SUN})}{T = 0 \, \text{SUN}} \times 100\%$$

The anabolic effects of the 3-carboxamide regioisomers (Compounds 2, 4, 6 and 8) at twenty-four hours after administration are significantly greater than the corresponding 5-carboxamide regioisomers (Compounds 1, 3, 5, and 7), as indicated by the change in serum urea nitrogen levels shown in Table 1. Compounds 2, 4, 6 and 8 also have modest lipolytic effects, as shown in Table 1 by the non-esterfied fatty acid levels fifteen minutes and twenty-four hours after administration.

The test described above was repeated with the 2-carboxamide regioisomers (Compounds 9–13) identified below. No corresponding 4-carboxamide regioisomers to Compounds 9–13 were utilized in this test. The results are shown below in Table 2:

TABLE 2

| STRUCTURE | ΔNEFA*<br>15 Min. | ΔNEFA<br>24 Hours | Δ% SUN*<br>24 Hours |
|---|---|---|---|
| 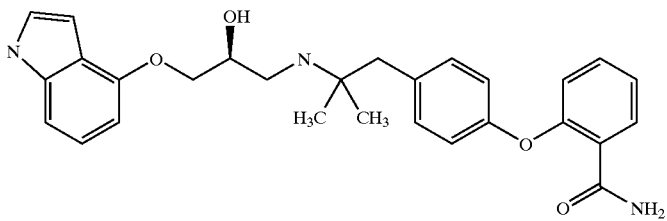<br>Compound 9 | 99 | −15.4 | −37 |

TABLE 2-continued

| STRUCTURE | ΔNEFA*<br>15 Min. | ΔNEFA<br>24 Hours | Δ% SUN*<br>24 Hours |
|---|---|---|---|
| 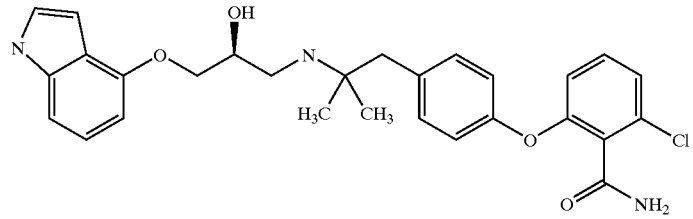<br>Compound 10 | 52.7 | −72.7 | −20.7 |
| 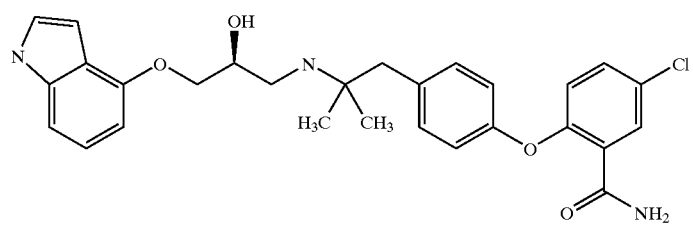<br>Compound 11 | 94 | −14.1 | −39.4 |
| 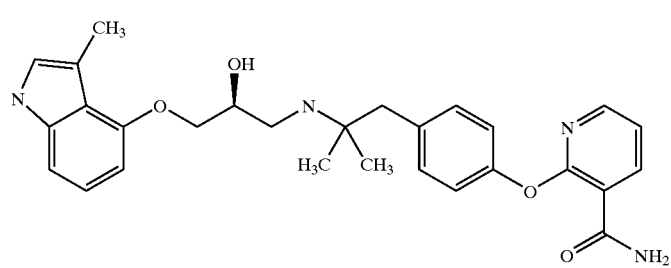<br>Compound 12 | 332.6 | −63.7 | −30.1 |
| 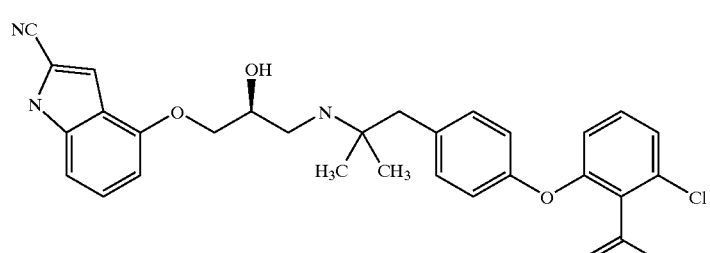<br>Compound 13 | 118.1 | 32.1 | −36.7 |

Based on the data provided in Tables 1 and 2, it has now been found that the presence of a carboxamide group at the two-position of Ring B in the aryloxy propanolamine represented by Structural Formula (I), shown hereinabove, results in a compound which is strongly anabolic. The corresponding regioisomer with the carboxamide group in the five-position is significantly less anabolic (Table 1). In addition, it has now been found that the presence of a carboxamide group at the three-position of Ring B in the, aryloxy propanolamine represented by Structural Formula (I), shown hereinabove, results in a compound which is modestly lipolytic. The corresponding regioisomer with carboxamide group in the five-position shows a much stronger lipolytic effect.

Example 18

Effect of Compound 6 on Muscle and Fat Content

Compound 6 was found to increase muscle and decrease fat content in a 28-day cattle study. Thirty-two Angus crossbred steers were blocked by weight into a heavy (4 heaviest blocks, avg. initial BW=1226 lb. (557 kg)) and a light (4 lightest blocks, avg. initial BW=1164 lb. (528 kg)) replication. The steers within each block were assigned to one of four treatments (8 steers/treatment) to investigate the effects of orally administered Compound 6 on the growth and carcass measurements when fed to cattle for 28 days immediately prior to slaughter. The treatments included a CONTROL (0.0 mg Compound 6 per kg BW), and three levels of Compound 6 (LOW, 0.125 mg Compound 6 per kg BW; MED, 0.250 mg Compound 6 per kg BW; HIGH, 0.500 mg Compound 6 per kg BW). Compound 6 was mixed with ground corn and fed to the steers as a top dress on a portion of their daily feed. The CONTROL steers received a similar amount of a ground corn top dress. The steers were required to consume the initial feed and top dress before the remaining amount of feed was issued. The basal ration was a commercially available feed (19.3% CP, DM basis). Both feed and water were available ad libitum. The steers were individually housed in 12 ft×48 ft pens equipped with an individual feed bunk and automatic waterer. On day 28 the steers were weighed and a blood sample collected prior to being shipped for slaughter and subsequent carcass evaluation.

Figure 2:
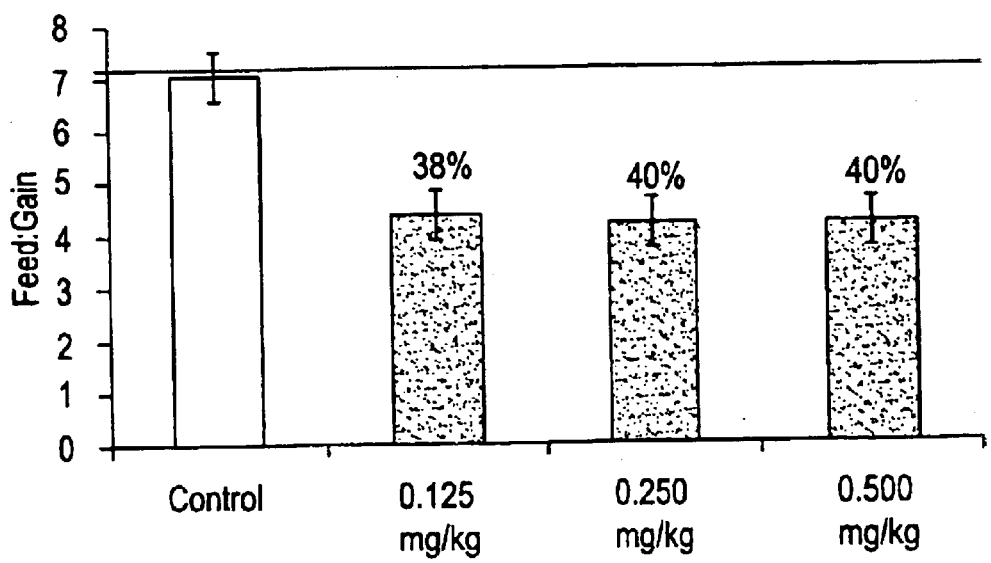
FIG. 2 is a graph showing the feed efficiency ratio after twenty-eight days for cattle treated with: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.

Live performance parameters were improved with the cattle on the Compound 6 treatments. LOW, MED, and HIGH exhibited a 54% to 73% increase in average daily gain (ADG, pounds/day) over CONTROL, specifically 6.31, 7.07, 6.74, and 4.08 pounds/day, respectively (2.86, 3.21, 3.06, and 1.85 kg/day); P<0.0002; FIG. 1. Daily dry matter intake did not differ (P>0.47) between the treatments. Feed efficiency (pound of feed per pound of gain) was improved (P<0.0006) on LOW, MED, HIGH compared to CONTROL (4.36, 4.19, 4.18, and 7.04, respectively; FIG. 2.

Figure 3:
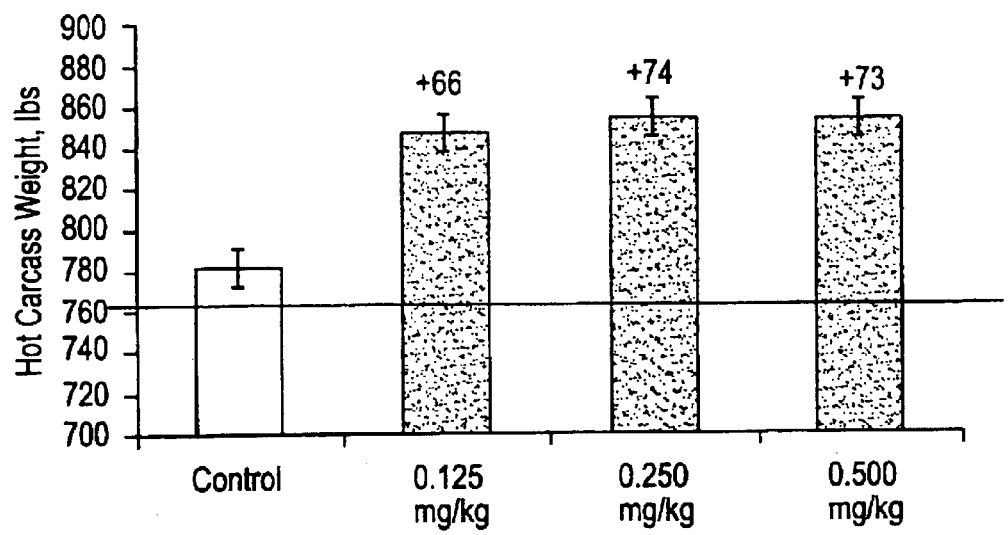
FIG. 3 is a graph showing the hot carcass weight for cattle treated with the following over a twenty-eight day period: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.
Figure 4:
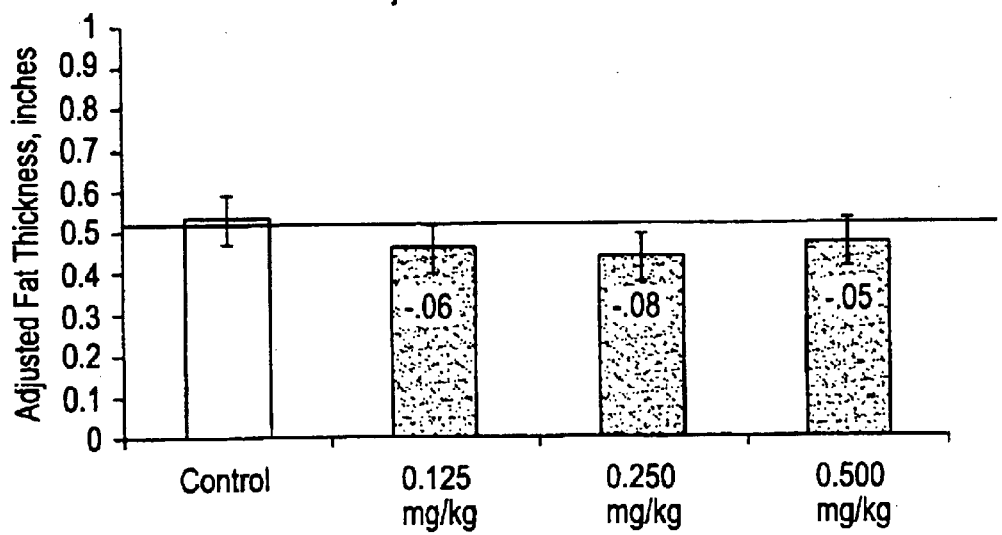
FIG. 4 is a graph showing the adjusted twelfth rib fat thickness of cattle treated with the following over a twenty-eight day period: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.
Figure 5:
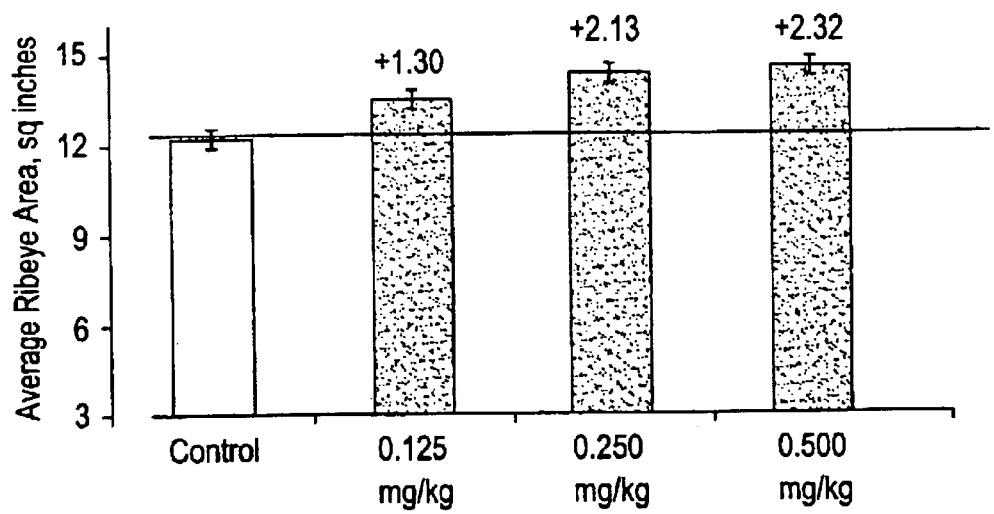
FIG. 5 is a graph showing the average ribeye area of cattle treated with the following over a twenty-eight day period: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.

The improved live weight gain was maintained in the carcass as evidenced by an increased (P<0.0001) hot carcass weight with LOW, MED, and HIGH compared to CONTROL, specifically 848, 855, 854, and 781 pounds (384, 388, 388, and 355 kg.), respectively. (FIG. 3). Dressing percent also tended (F-test P=0.1138, Treatment P<0.05) to be higher with the Compound 6 treatments, and the orthogonal comparison showed a significant (P<0.0043) low dose plateau response with the addition of Compound 6. Fat thickness at the twelfth rib was not different (P>0.78; FIG. 4), but the area of the longissimus dorsi muscle at the twelfth rib was 10.7 to 18.9% larger (P<0.0068) with LOW, MED, and HIGH compared to CONTROL (13.5, 14.3, 14.5, 12.2 in$^2$, respectively; FIG. 5).

Figure 6:
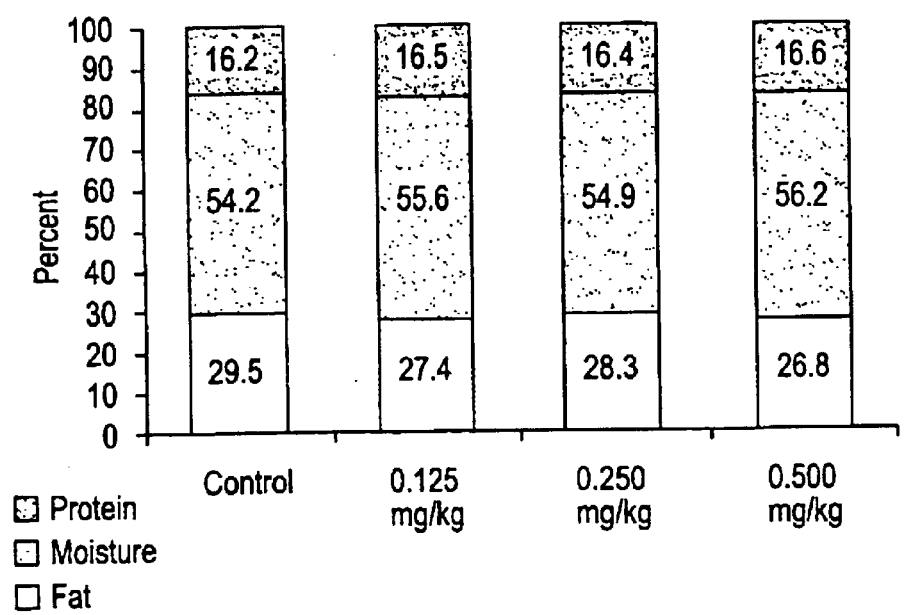
FIG. 6 is a graph showing the carcass soft tissue composition of cattle treated with the following over a twenty-eight day period: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.

Carcass composition including % fat, % protein, % moisture, and % bone were calculated using the equations, reported by Hankins, O. G., and Howe, P. E. 1946. U.S. Department of Agriculture Technical Bulletin No. 926 pp. 1–20 (FIG. 6). The carcass composition did not differ statistically (P>0.12) among the treatments for any of the components, but % fat was numerically (~1.2 to ~2.7%) less with the Compound 6 treatments than CONTROL. However, because of the heavier carcass weights observed with the LOW, MED, and HIGH treatments, the calculated yield or pounds of protein and moisture (FIG. 6) were significantly greater (P<0.0036) than CONTROL (Protein— 115.8, 115.1, 115.8, 103.1 pounds, (52.6, 52.3, 52.6, 46.8 kg) respectively; moisture—389.2, 384.7, 393.4, 345.3 pounds, (176.7, 174.7, 178.6, 156.8 kg) respectively).

Figure 7:
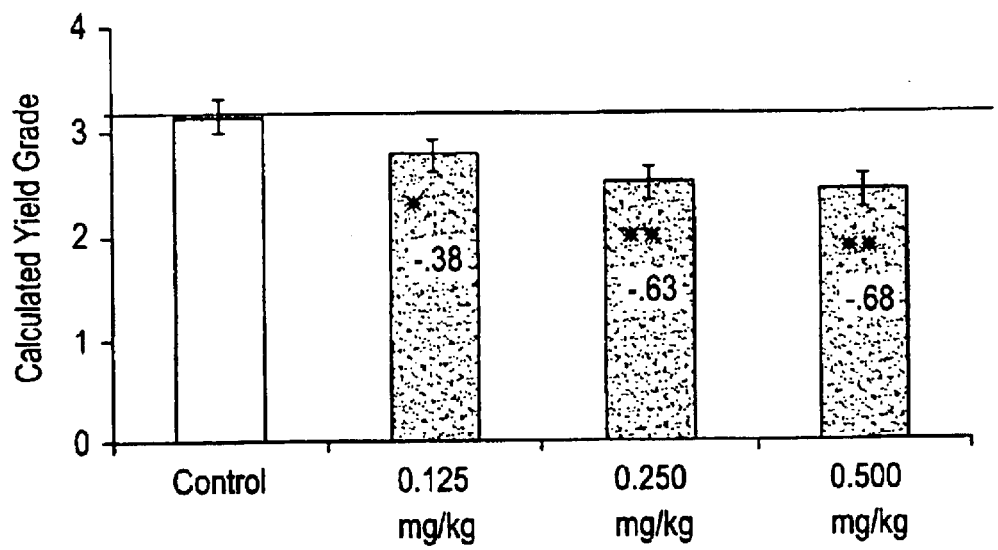
FIG. 7 is a graph showing the calculated yield grade of meat obtained from cattle treated with the following over a twenty-eight day period: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.
Figure 8:
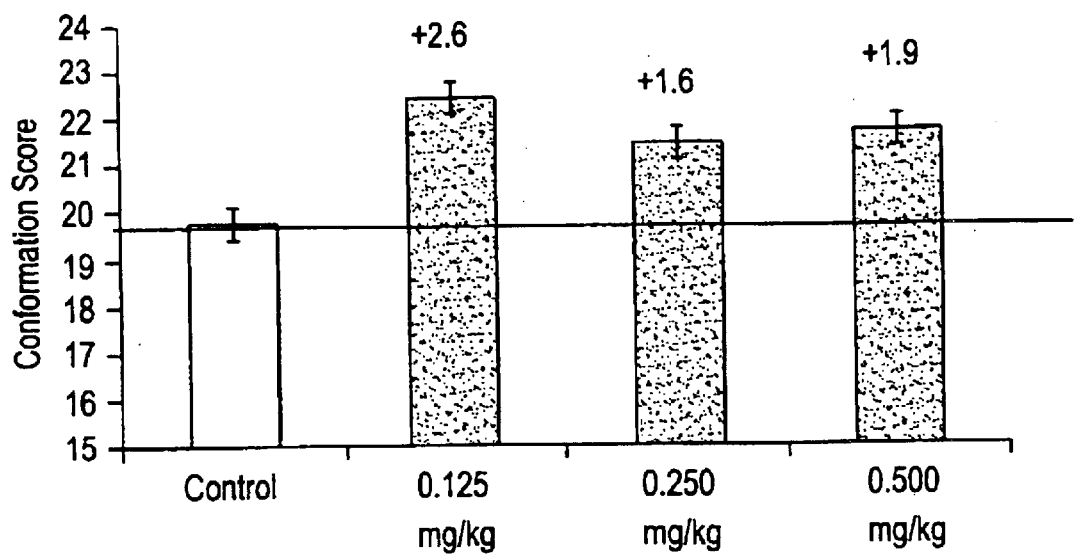
FIG. 8 is a graph showing the conformation score of meat obtained from cattle treated with the following over a twenty-eight day period: a) 0.0 mg of Compound 6 per kilogram of body weight per day; 0.125 mg of Compound 6 per kilogram of body weight per day; 0.250 mg of Compound 6 per kilogram of body weight per day; and 0.5 mg of Compound 6 per kilogram of body weight per day.

A meat scientist evaluated the carcasses and determined the United States Department of Agriculture (USDA) quality grade and marbling scores. Neither the USDA quality grade nor marbling scores differed among the treatments (P>0.90). Yield grade (YG) values (FIG. 7) were calculated using measurements from the necessary components. YG is an indicator of the amount of retail meat cuts with a lower value indicating a greater amount of high-valued saleable meat. YG tended (F-test P=0.0632; Treatment P<0.09) to be lower for the three Compound 6 treatments than CONTROL. Orthogonal analysis comparing CONTROL, LOW, MED and HIGH, indicated YG decreased linearly with increasing Compound 6 doses eventually plateauing at MED and HIGH (P=0.0021; 3.14, 2.76, 2.51, and 2.46, respectively). Conformation score (FIG. 8) which is a subjective measure of muscling was higher (P<0.005) for Compound 6 treatments than CONTROL indicating carcasses on the Compound 6 treatments exhibited thicker, more pronounced muscling than CONTROL carcasses.

Meat quality was investigated using several different measurements on longissimus dorsi strip steaks. There were no treatment differences (P>0.5) in color as measured by Hunter a*, b*, and L*, or pH measured after a 14 day post-mortem aging time. Subjective color, texture, and firmness measurements of the longissimus dorsi muscle at the twelfth rib approximately 24 hour post-mortem also showed no treatment differences (F-test P>0.07).

Warner-Bratzler shear force, (National Cattlemen's Association, "Standardized Warner-Bratzler Shear Force Procedures for Genetic Evaluation" (1994); see also Wheeler et al., J. Animal Sci., 75, 2423–2432, (1997)), a mechanical predictor of "tenderness" (a lower value is more tender) was measured on steaks aged 14 days. In a comparison of CONTROL, LOW, MED, and HIGH, the shear values from steaks aged 14 days (2.25, 2.92, 2.55 and 3.01 kg, respectively) were not different (F-test P=0.106). Orthogonal contrasts of these four treatments showed a low-dose plateau response (P=0.0294). Although steaks from steers treated with Compound 6 had numerically higher shear values, the observed shear values were within the range of 2.27 to 3.58 kg which Boleman et al., 1997. J. Anim. Sci. 75:521–1524 considered as "tender" and were less than the 5.90 kg needed to be considered "tough".

In conclusion, feeding Compound 6 to these steers resulted in improved efficiency of gain due to 54 to 73% greater weight gain on the same amount of feed. The higher live weight gain was maintained in the carcass as evidenced by heavier hot carcass weights. The extra carcass weight was due primarily to an increased amount of muscling. The large increase in muscling was observed without any apparent deleterious effects on the quality of the meat as determined by carcass marbling scores, and color, pH, and Warner-Bratzler shear force of strip steaks aged for fourteen days.

Example 19

Effect of Compound 6 on Weight Gain and Feed Efficiency During the Last 14 Days of the Growing Period in Broiler Chickens Approximately 1500 Peterson-Hubbard, day-old, male chicks were used in a randomized, complete-block design with 4 treatments (Control, Clenbuterol at 1 PPM, and Compound 6 at 3 and 15 PPM (mg/kg feed)). The testing facility contained 36 pens, divided equally into 6 blocks. Treatments were randomly allotted to pens within each block. Each treatment consisted of 6 pens with 10 birds per pen.

Day-of-age birds were obtained from Pine Manor Hatchery in Goshen, Ind. Approximately 40 birds per pen were set at random upon receipt. On day 30 of the growout period, all birds were weighed and the 15 birds closest to the block mean were selected. These birds were allowed to acclimate until day 35 of age. On that day, all remaining birds were weighed again, and the 10 birds/pen closest to the block mean were chosen for the treatment phase. Birds were provided ad libitum access to feed and water throughout the trial. All birds were fed a 23% crude protein corn-soy ration from day 1 until day 18 of age. The feed was changed to a 20% crude protein corn-soy ration from day 18 to day 49. The treatment feed was mixed using the same 20% crude protein basal ration. Treatments were administered in the feed from day 35 through day 49. Feed consumption was calculated over the entire 14-day treatment period. Birds were weighed at trial completion (day 49), and transported to Purdue University, West Lafayette, Ind. 47907, U.S.A. meat laboratory for slaughter and carcass measurements on day 50. Weights of the hot carcass, fat pad, and viscera were taken on all animals.

The results of the study are summarized in Table 3. As demonstrated by the data, Compound 6 compares favorably with clenbuterol in increasing weight gain and improving feed efficiency during the last 14 days of the growing period in broiler chicks. Compound 6 showed an increase in weight gain of 3.17% (P=0.0987) over control for the 3 PPM treatment, and a 3.17% (P=0.0756) increase over control for the 15 PPM treatment. The clenbuterol-treated birds showed a 2.38% (P=0.1430) increase over control during the 14-day treatment period. Compound 6 improved feed efficiency by 2.50% (P=0.2936) at the 3 PPM-treatment level and by 3.00% (P=0.1957) at the 15 PPM-treatment level. The clenbuterol-treated animals showed an improvement in feed conversions of 0.50% (P=0.7320) versus control.

The effect of the high dose of the experimental compound on weight gain and feed efficiency prompted carcass evaluations at Purdue University. Hot carcass, viscera, and fat pad weights were taken on all treatments. Hot carcass weights were increased in both treatments with the experimental compound compared to control. Compound 6 treatments increased hot carcass weights by 2.50% (P=0.0174) and 2.82% (P=0.0078) for the 3 PPM and 15 PPM treatments, respectively. The clenbuterol treatment increased hot carcass weights by 3.25% (P=0.0027). Viscera weights decreased with respect to control for both treatments with the experimental compound. Compound 6 decreased viscera weights by 1.50% (P=0.3981) and 0.65% (P=0.7279) for the 3 PPM and 15 PPM treatments, respectively. Clenbuterol reduced viscera weight by 0.66% (P=0.7215). A trend was also observed towards increased fat pad weights for both treatments. The Compound 6 treatments increased fat pad weight by 9.68% (P=0.1069) and 4.09% (P=0.4814) for the 3 PPM and 15 PPM treatments, respectively.

PPM (mg/kg feed)). The testing facility contained two wings, each containing 30 pens. The pens in each wing were divided into 6 blocks of 5 pens. Treatments were randomly allotted within each block. Each treatment consisted of 12 pens with 10 birds per pen.

Day-of-age birds were obtained from Pine Manor Hatchery in Goshen, Ind. Approximately 40 birds per pen were set at random upon receipt. On day 16 of the growout period, all birds were weighed and the 15 birds closest to the block mean were selected. These birds were allowed to acclimate until day 21 of age. On this day, all remaining birds were weighed again, and the 10 birds/pen closest to the block mean were chosen for the treatment phase. Birds were provided ad libitum access to feed and water throughout the trial. All birds were fed a 23% crude protein corn-soy ration from day 1 until day 18 of age. The feed was changed to a 20% crude protein ration for day 18 to day 49. The treatment feed was mixed using the 20% crude protein basal ration. Treatments were administered in the feed from day 21 through day 49. An interim weight was taken on day 35. Feed consumption was calculated over the entire 28-day treatment period. Birds were weighed at trial completion (day 49), and were transported to Purdue University meat laboratory for slaughter and carcass measurements on day, 50. Weights of the hot carcass; fat pad; viscera; bone-in, skin-on breast; and bone-in, skin-on, leg quarter were taken on all animals.

The results of the study are summarized in Table 4. Birds treated with Compound 6 at 3 PPM showed a 3.22% (P=0.0395) increase in weight gain over control during the first 14 days of the treatment period. The 15 PPM-treatment showed a 1.08% (P=0.7600) increase over control during the same period. During last 14 days of treatment, Compound 6 showed increased responses of 6.67% (P=0.0064) and 1.90% (P=0.5028) for the 3 PPM and 15 PPM doses, respectively. Over the entire 28-day treatment period, Compound 6 gave 5.03% (P=0.0051) and 1.01% (P=0.5419) increases in weight gain for the 3 PPM and 15 PPM doses, respectively.

TABLE 3

Growth Performance and Carcass Characteristics

| Treatment | Dose | Initial Weight (kg) | Final Weight (kg) | Total 14 day Weight Gain (kg) | Pen Feed Intake (kg) | Feed Efficiency F/G | Dressing Percentage | Hot Carcass Weights (g) | Viscera Weight (g) | Fat Pad Weight (g) |
|---|---|---|---|---|---|---|---|---|---|---|
| Control | 0 PPM | 1.72 | 2.98 | 1.26 | 25.16 | 2.00 | 71.83 | 2122.71 | 287.36 | 26.14 |
| Clenbuterol | 1 PPM | 1.73 | 3.02 | 1.29 | 25.20 | 1.99 | 72.77** | 2191.64** | 285.45 | 26.86 |
| Compound 6 | 3 PPM | 1.72 | 3.02 | 1.30 | 25.74 | 1.95 | 72.43* | 2175.69* | 283.04 | 28.67 |
| Compound 6 | 15 PPM | 1.72 | 3.02 | 1.30 | 25.25 | 1.94 | 72.63** | 2182.55** | 285.49 | 27.21 |

(60 birds/treatment) 6 pens/treatment, 10 birds/pen, Peterson × Hubbard birds
14 day treatment period (day 35–49)
F/G is pen feed intake/total pen weight
20% crude protein diet
(*P < .05) and (**P < .01) indicate difference from control Example 20
Effect of Compound 6 on Weight Gain, Feed Efficiency, and Breast and Leg Quarter Weights During the Last 28 Days of the Growing Period in Broiler Chickens Approximately 2500 Peterson-Hubbard, day-old, male chicks were used in a randomized, complete-block design with 3 treatments (Control and Compound 6 at 3 and 15

Feed efficiency, when measured as feed/gain, showed a trend for improvement in both treatments over the 28-day treatment period. Compound 6 showed improvements of 6.85% (P=0.1426) and 4.57% (P=0.3594) for the 3 PPM and 15 PPM treatments, respectively, when compared with control.

Carcass evaluation of the hot carcass weights showed significant increases over control animals. Compound 6 treated animals showed an increase of 6.50% (P=0.0001) and 2.90% (P=0.0434) for the 3 PPM and 15 PPM treatments, respectively. The fat pad (including both abdominal fat and gizzard fat) was stripped from each bird and weighed to determine the effect of these compounds on fat accretion. Compound 6 showed no significant effect at either dose. Each of the treatments demonstrated a trend for decreased viscera weights when compared to control. Compound 6 showed a 1.54% (P=0.4004) and 3.29% (P=0.0764) decrease for the 3 PPM and 15 PPM treatments, respectively.

The breast muscle was weighed with the bone and skin attached. A 4.00% (P=0.0227) increase was observed in the low dose of Compound 6 while the high dose exhibited a 1.06% (P=0.5351) increase. Bone-in, skin-on, leg quarters also showed highly significant increases with the Compound 6 treatments (i.e. 10.63% (P=0.0001) and 5.60% (P=0.0003) for 3 PPM and 15 PPM treatments, respectively).

In conclusion, oral administration of Compound 6 did not significantly increase weight gain in male broilers when fed from day 21–35 of their life cycle. However, Compound 6 at 3 PPM significantly increased (P<0.01) weight gain during days 35–49. The increase was also significant (P<0.01) when analyzed during the entire 28-day feeding period. A trend was observed towards improved feed efficiency in all treatments during the entire 28-day feeding period. All doses exhibited significant (P<0.05) increases in hot carcass weights. At both doses, Compound 6 showed highly significant increases in bone-in, skin-on leg-quarter weights (P<0.01). Compound 6 showed a significant increase in bone-in, skin-on, breast weight (P<0.05) at the 3 PPM dose.

The following formulation examples are illustrative only and are not intended to limit the scope of the invention in any way. "Active Ingredient," of course, means a compound of Structural Formula I or a physiologically acceptable salt or solvate thereof.

Example 21

Premix for Chickens

| Ingredient | % by weight |
|---|---|
| Active Ingredient | 25 |
| Ground Corn | 74 |
| Sodium Chloride | 1 |
| | 100 |

Example 22

Premix for Ruminants

| Ingredient | % by weight |
|---|---|
| Active Ingredient | 30 |
| Ground yellow corn | 60 |
| Alfalfa meal | 10 |
| | 100 |

TABLE 4

Growth Performance and Carcass Characteristics

| Treatment | Dose (PPM) | Initial Weight (kg) Day 21 | Interim Weight (kg) Day 35 | Final Weight (kg) Day 49 | Weight Gain Period 1 (kg) (d 21–35) | Weight Gain Period 2 (kg) (d 35–49) | Total Weight Gain (kg) (d 21–49) | Pen Feed Intake (kg) | Feed Efficiency F/G | Dressing Percentage | Hot Carcass Weight (g) |
|---|---|---|---|---|---|---|---|---|---|---|---|
| Control | 0 | 0.69 | 1.62 | 2.68 | 0.93 | 1.05 | 1.99 | 39.98 | 2.19 | 69.85 | 1873.81 |
| Compound 6 | 3 | 0.69 | 1.66* | 2.78** | 0.96* | 1.12** | 2.09** | 41.22 | 2.04 | 71.14** | 1995.58** |
| Compound 6 | 15 | 0.69 | 1.63 | 2.70 | 0.94 | 1.07 | 2.01 | 39.09 | 2.09 | 71.16** | 1928.17* |

| Treatment | Dose (PPM) | Viscera Weight (g) | Fat Pad Weight (g) | Bone-in, Skin-on Breast Weight (g) | Bone-in, Skin-on leg Quarter Weight (g) |
|---|---|---|---|---|---|
| Control | 0 | 269.97 | 50.71 | 594.28 | 601.67 |
| Compound 6 | 3 | 265.82 | 51.67 | 618.03* | 665.64** |
| Compound 6 | 15 | 261.08 | 49.16 | 600.55 | 635.36** |

(120 birds/treatment) 12 pens/treatment, 10 birds/pen, Peterson x Hubbard birds
28 day treatment period (day 21–49)
F/G is pen feed intake/total pen weight
20% crude protein corn-soy diet
(*P < .05) and (**P < .01) indicate difference from control

Example 23

Premix for Swine

| Ingredient | % by weight |
|---|---|
| Active Ingredient | 10 |
| Soybean mill run | 88 |
| Mineral oil | 2 |
| | 100 |

The above ingredients are blended to uniformity to provide a dry flowable premix that can be admixed with at typical animal feed ration at a rate to provide about 20 ppm of active ingredient in the final feed ration. For example, the premix can be added to the following swine grower ration for convenient oral administration of the Active Ingredient to swine.

| Ingredient | % by weight | Lbs/Ton |
|---|---|---|
| Corn, yellow, ground | 76.70 | 1534 |
| Soybean Oil Meal, solvent extracted, dehulled | 19.35 | 387 |
| Calcium Carbonate | 1.20 | 24 |
| Dicalcium Phosphate, feed grade | 1.20 | 24 |
| Salt (sodium chloride) | 0.50 | 10 |
| Trace mineral premix, AN-03[1] | 0.10 | 2 |
| Swine Vitamin Premix, SW-03[2] | 0.65 | 13 |
| Vitamin A Premix, 3M USP units/lb.[3] | 0.05 | 1 |
| Methionine Hydroxy Analogue, 93% | 0.20 | 4 |
| Selenium Premix[4] | 0.005 | 1 |
| | 100.00 | 2000 |

[1]Each Kg of premix contains: 50 g. manganese as manganese sulfate; 100 g. zinc as zinc carbonate; 50 g. iron as ferrous sulfate; 5 g. copper as copper oxide; 1.5 g. iodine as potassium iodide and 150 g. maximum and 130 g. minimum calcium as calcium carbonate.
[2]Each Kg of premix contains: 77,161 IU Vitamin D2; 2,205 IU Vitamin E; 411 mg. riboflavin; 1,620 mg. pantothenic acid; 2,205 mg. niacin; 4.4 mg. Vitamin B12; 441 mg. Vitamin K; 19,180 mg. choline; 110 mg. folic acid; 165 mg. pyridoxine; 110 mg. thiamine; 22 mg. biotin.
[3]Each Kg of premix contains 6,613,800 IU Vitamin A.
[4]Each Kg of premix contains 200 mg. of selenium as sodium selenite.

Example 24

Feed Ration for Lambs

| Ingredient | Percent | Lbs/T |
|---|---|---|
| Yellow corn | 61.00 | 1220.0 |
| Corn cobs | 20.00 | 400.0 |
| Alfalfa Meal, dehydrated | 5.40 | 108.0 |
| Soybean oil meal | 8.00 | 160.0 |
| Urea, feed grade | 0.50 | 10.0 |
| Molasses, cane | 3.00 | 60.0 |
| Dicalcium phosphate | 0.43 | 8.6 |
| Salt | 0.30 | 6.0 |
| Calcium carbonate | 0.14 | 2.3 |
| Trace mineral premix[1] | 0.03 | 0.6 |
| Vitamin A + D[3] Premix[2] | 0.10 | 2.0 |

-continued

| Ingredient | Percent | Lbs/T |
|---|---|---|
| Vitamin E Premix[3] | 0.10 | 2.0 |
| Active Ingredient | 1.00 | 20.0 |
| | 100.00 | 2000.0 |

[1]Trace mineral premix contains: 2.5% manganese as manganese oxide, 0.07% iodine as potassium iodide, 0.3% cobalt as cobalt carbonate, 0.5% copper as copper oxide, and 20.0% zinc as zinc sulfate.
[2]Each pound of vitamin A and D3, premix contains 2,000,000 USP units Vitamin A and 225,750 USP units Vitamin D3.
[3]Each pound of Vitamin E premix contains 20,000 IU Vitamin E.

Example 25

Broiler Finisher Ration

| Ingredients | % by weight | Lbs/T |
|---|---|---|
| Ground yellow corn | 66.40 | 1328.00 |
| Animal-vegetable fat | 1.53 | 30.60 |
| Corn Glut. meal (60%) | 4.00 | 80.00 |
| Soybean meal (48%) | 19.19 | 383.80 |
| Fish meal-menhaden | 2.50 | 50.00 |
| Dicalcium phosphate | 1.01 | 34.20 |
| Feather meal-Hydr. | 2.50 | 50.00 |
| Ground limestone | 0.83 | 16.60 |
| Salt | 0.30 | 6.00 |
| Vitamin Premix[1] | 0.50 | 10.00 |
| Trace mineral premix[2] | 0.10 | 2.00 |
| Methionine Hyd. Anal. | 0.15 | 3.00 |
| Lysine HCl | 0.29 | 5.80 |
| | 100.00 | 2000.00 |

[1]Vitamin premix provides 3000 IU of vitamin A, 900 ICU of vitamin D3, 40 mg of vitamin E, 0.7 mg of vitamin K, 1000 mg of choline, 70 mg of niacin, 4 mg of pantothenic acid, 4 mg of riboflavin, 100 mcg of vitamin $B_{12}$, 100 mcg of biotin and 125 mg of ethoxyquin per kg of complete feed.
[2]Trace mineral premix provides 75 mg of manganese, 50 mg of zinc, 25 mg of iron and 1 mg of iodine per kg of complete feed.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A compound represented by the following structural formula:

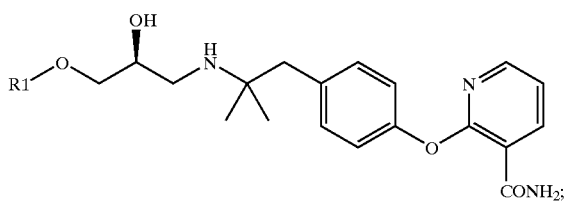

or a physiologically acceptable salt thereof, wherein R1 is represented by a structural formula selected from the group consisting of:

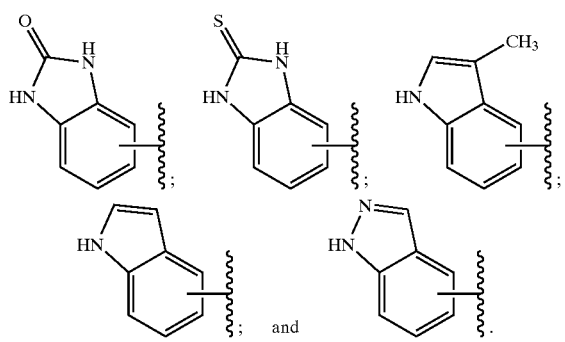

2. A compound represented by the following structural formula:

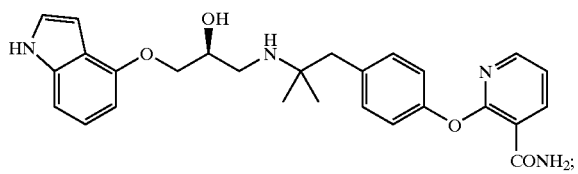

or a physiologically acceptable salt thereof.

3. The ammonium chloride, ammonium oxalate, ammonium acetate or ammonium 4-hydroxybenzoate salt of the compound of claim 2.

4. A method of promoting growth, efficiency of feed utilization and/or production of lean body mass in a livestock animal, comprising administering to the animal an effective amount of a compound represented by the following structural formula:

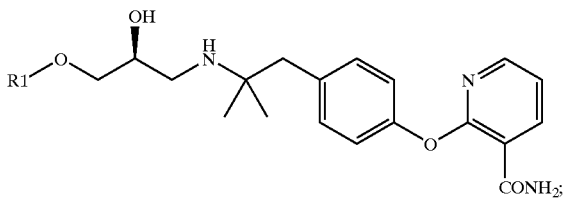

or a physiologically acceptable salt thereof, wherein R1 is represented by a structural formula selected from the group consisting of:

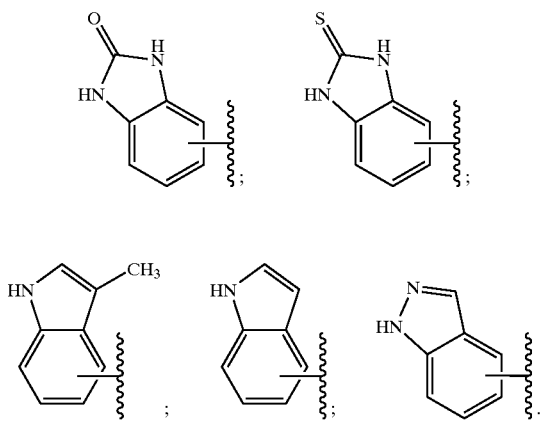

5. The method of claim 4 wherein the animal is a ruminant.

6. The method of claim 5 wherein the ruminant is a cow, bull, heifer or steer.

7. The method of claim 4 wherein the animal is an avian.

8. The method of claim 7 wherein the avian is a chicken, turkey or duck.

9. A method of promoting growth, efficiency of feed utilization and/or production of lean body mass in a livestock animal, comprising administering to the animal an effective amount of a compound represented by the following structural formula:

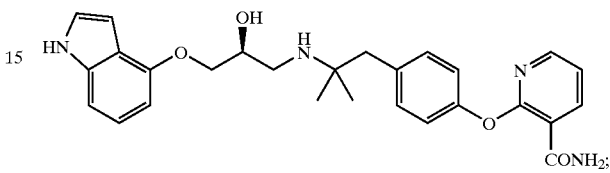

or a physiologically acceptable salt thereof.

10. The method of claim 9 wherein the animal is a ruminant.

11. The method of claim 10 wherein the ruminant is a cow, bull, heifer or steer.

12. The method of claim 11 comprising administering the ammonium chloride, ammonium oxalate, ammonium acetate or ammonium 4-hydroxybenzoate salt of the compound.

13. The method of claim 9 wherein the animal is an avian.

14. The method of claim 13 wherein the avian is a chicken, turkey or duck.

15. The method of claim 14 comprising administering the ammonium chloride, ammonium oxalate, ammonium acetate or ammonium 4-hydroxybenzoate salt of the compound.

16. A method of increasing the quantity of meat or improving the quality of meat obtained from a livestock animal, comprising administering to the animal an effective amount of one or more compounds represented by the following structural formula:

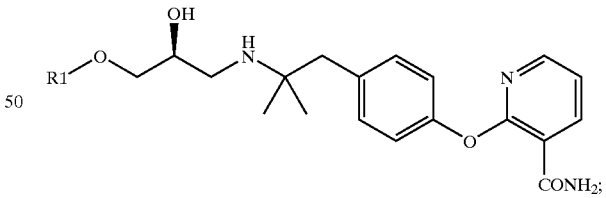

or a physiologically acceptable salt thereof, wherein R1 is represented by a structural formula selected from the group consisting of:

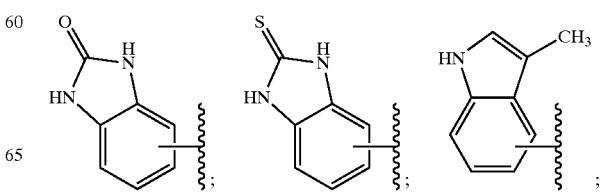

-continued

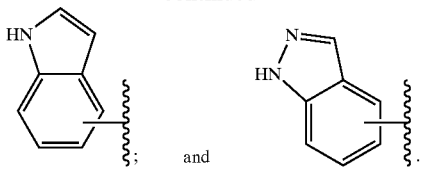
and

17. A method of increasing the quantity of meat or improving the quality of meat obtained from a livestock animal, comprising administering to the animal an effective amount of one or more compounds represented by the following structural formula:

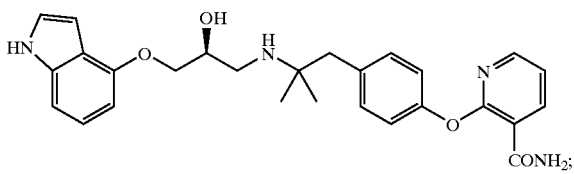

or a physiologically acceptable salt thereof.

18. The method of claim 17 comprising administering the ammonium chloride, ammonium oxalate, ammonium acetate or ammonium 4-hydroxybenzoate salt of the compound.

19. An animal feed premix comprising a compound of Structural Formula I, as defined in claim 1, or a physiologically acceptable salt or solvate thereof, in association with a suitable carrier therefor.

20. An animal feed premix as claimed in claim 19, wherein the compound is

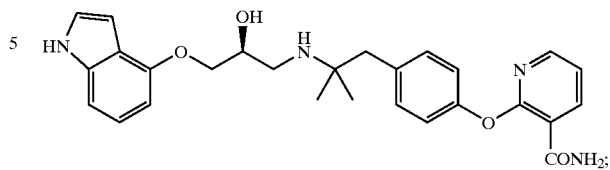

or a physiologically acceptable salt or solvate thereof.

21. An animal feed composition comprising a compound of Structural Formula I, as defined in claim 1, or a physiologically acceptable salt or solvate thereof, in association with a suitable carrier therefor.

22. An animal feed composition as claimed in claim 21, wherein the compound is

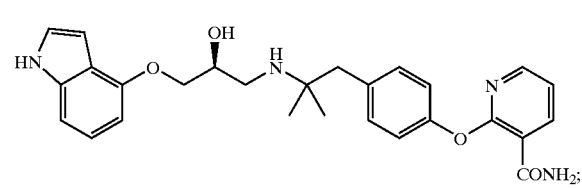

or a physiologically acceptable salt or solvate thereof.

* * * * *